: (12) United States Patent
Schiemann et al.

(10) Patent No.: US 9,527,850 B2
(45) Date of Patent: Dec. 27, 2016

(54) BENZYL PIPERIDINE COMPOUNDS AS LYSOPHOSPHATIDIC ACID (LPA) RECEPTOR ANTAGONIST

(75) Inventors: Kai Schiemann, Seeheim-Jugenheim (DE); Wolfgang Staehle, Ingelheim (DE); Michael Busch, Darmstadt (DE); Dirk Wienke, Darmstadt (DE); Oliver Poeschke, Wiesbaden (DE); Christa Burger, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/344,267

(22) PCT Filed: Sep. 7, 2012

(86) PCT No.: PCT/EP2012/003771
§ 371 (c)(1),
(2), (4) Date: Jun. 6, 2014

(87) PCT Pub. No.: WO2013/045028
PCT Pub. Date: Apr. 4, 2013

(65) Prior Publication Data
US 2015/0011557 A1 Jan. 8, 2015

(30) Foreign Application Priority Data
Sep. 26, 2011 (EP) .................................. 11007796

(51) Int. Cl.
| C07D 401/14 | (2006.01) |
| A61K 31/45 | (2006.01) |
| C07D 487/04 | (2006.01) |
| C07D 403/04 | (2006.01) |
| C07D 471/04 | (2006.01) |
| A61K 31/4525 | (2006.01) |
| A61K 31/4535 | (2006.01) |
| A61K 31/454 | (2006.01) |
| A61K 31/4545 | (2006.01) |
| A61K 31/4985 | (2006.01) |
| C07D 401/04 | (2006.01) |
| C07D 405/04 | (2006.01) |
| C07D 409/04 | (2006.01) |

(52) U.S. Cl.
CPC ........... *C07D 487/04* (2013.01); *A61K 31/454* (2013.01); *A61K 31/4525* (2013.01); *A61K 31/4535* (2013.01); *A61K 31/4545* (2013.01); *A61K 31/4985* (2013.01); *C07D 401/04* (2013.01); *C07D 401/14* (2013.01); *C07D 403/04* (2013.01); *C07D 405/04* (2013.01); *C07D 409/04* (2013.01); *C07D 471/04* (2013.01)

(58) Field of Classification Search
CPC ... C07D 401/00; C07D 401/04; C07D 401/14; A61K 31/44

USPC .......................................... 546/201; 514/300
See application file for complete search history.

(56) References Cited

U.S. PATENT DOCUMENTS 5,322,850 A * 6/1994 Orjales-Venero .... C07D 401/04
514/322
2009/0005416 A1 1/2009 Munchhof et al.

FOREIGN PATENT DOCUMENTS

| EP | 1695955 A1 | 8/2006 |
| FR | 1173138 | 2/1959 |
| FR | 70999 | 9/1959 |
| FR | 2666582 | * 3/1992 |
| GB | 804786 | * 12/1956 |
| WO | 2009102574 A1 | 8/2009 |
| WO | 2010063352 A1 | 6/2010 |
| WO | 2010115491 A2 | 10/2010 |

OTHER PUBLICATIONS

CA53 "Piperidinylindoles" CA53 (1959).*
Fells et al. "Structure-based drug design . . . " Bioorg. Med. Chem. 17(21) 7457-7564 (2009).*
Heasley et al. "Initial structure-activit . . . " Bioorg. Med. Chem. Lett. 14 p. 2735-2740 (2004).*
Helsley "Analgesic and . . . " CA77:164705 (1972).*
Ravula et al. "Lead optimization of 2-piperidin . . . " Bioorg. Med. Chem. Lett. 22 p. 421-426 (2012).*
Schenker et al. "Tetrahydropyridine- . . . " CA82:43186 (1975).*
Van Duyne et al. "Effect of mimetic . . . " CA158:319358 (2013).*
Jin et al. "SDynthesis of 2-hetero . . . " Tetrahedron Lett. 56 p. 2720-2723 (2015).*
Aurelio et al. "New piperidine . . . " CA120:270389 (1994).*
Aurelio et al. "Synthesis and structure . . . " CA124:8747 (1995).*
Arran et al. "4-imidazolyl . . . " CA106:84602 (1987).*
Bartolome "Preparation of indole . . . " CA142:38264 (2004).*
Binet et al. "Preparation of 2- . . . " CA118:6986 (1993).*
Borstrom et al. "A pharmacophore . . . " CA134:202631 (2001).*
DAlessandro et al. "The identification . . . " CA152:206118 (2009).*
Goldbarb "Method of using . . . " CA151:92837 (2009).*
Hembrough et al. "Composition and methods . . . " CA147:134403 (2007).*
Improper Markus, Fed. Reg. 76(27) 7162-75, slides 1, 64-67 (2011).*
Lavrado et al. "The discovery and structure . . . " Bioorg. Med. Chem. Lett 20:2916-19 (2010).*
New Matter,US PTO connection, II(1) p. 1-3 (2005).*
Orjales et al. "Synthesis and . . . " CA124:8747 (1995).*
Owen et al. "Preparation of benz . . . " CA142:134613 (2005).*

(Continued)

*Primary Examiner* — Celia Chang
(74) *Attorney, Agent, or Firm* — Dwight D. Kim; EMD Serono Research and Development Institute

(57) ABSTRACT

The invention provides novel substituted benzyl piperidine compounds according to Formula (I) as lysophosphatidic acid (LPA) receptor antagonists, their manufacture and use for the treatment of proliferative or inflammatory diseases, such as cancer, fibrosis or arthritis.

16 Claims, No Drawings

(56) References Cited

OTHER PUBLICATIONS

Schenker et al. "Tetrhydorpyridin . . . " CA 82:43186 (1975).*
Stoit et al. "7-azaindole . . . " CA148:285076 (2008).*
Takayama et al. "Preparation of benimi . . . " CA134:252339 (2001).*
Fischer et al. "Structure-activity . . . " European J. Pharmcol. 350:353-361 (1998).*

* cited by examiner

BENZYL PIPERIDINE COMPOUNDS AS LYSOPHOSPHATIDIC ACID (LPA) RECEPTOR ANTAGONIST

RELATED APPLICATIONS

This application is a U.S. national stage application of PCT international application PCT/EP2012/003771, filed on Sep. 7, 2012, which claims the benefit of European application no. 11007796.3, filed on Sep. 26, 2011. The entire contents of the aforementioned applications are hereby incorporated by reference.

FIELD OF THE INVENTION

The invention relates to a series of novel substituted benzyl piperidine compounds that are useful in the treatment of proliferative or inflammatory diseases, such as cancer, fibrosis or arthritis in mammals. Also encompassed by the present invention is the use of such compounds in the treatment of proliferative or inflammatory diseases in mammals, especially humans, and pharmaceutical compositions containing such compounds.

SUMMARY OF THE RELATED ART

Lysophospholipids are membrane-derived bioactive lipid mediators. Lysophospholipids affect fundamental cellular functions that include proliferation, differentiation, survival, migration, adhesion, invasion, and morphogenesis. These functions influence many biological processes that include, but are not limited to, neurogenesis, angiogenesis, wound healing, fibrosis, immunity, inflammation, and carcinogenesis.

Lysophosphatidic acid (LPA) is a lysophospholipid that has been shown to act through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses. Antagonists of the LPA receptors find use in the treatment of diseases, disorders or conditions in which LPA plays a role, especially in proliferative or inflammatory diseases, such as cancer, fibrosis or arthritis.

In ascites and plasma of ovarian cancer patients increased LPA levels were detected. LPA has been shown to promote tumor cell proliferation, survival, migration and invasion. Increased levels of LPA, altered receptor expression and altered responses to LPA may contribute to the initiation, progression or outcome of ovarian cancer. LPA is potentially also involved many other types of cancer, such as prostate, breast, melanoma, head and neck, bowel and thyroid cancers. Therefore, a LPA receptor antagonist (preferably subtype selective) should be able to decrease these effects, most likely resulting in a positive outcome in cancer progression. LPA primarily exert its biological effects via G protein-coupled receptors, such as EDG-2/LPA1, EDG-4/LPA2, EDG-7/LPA3, GPR23/LPA4, GPR93/LPA5, p2y5/LPA6. Especially EDG-4/LPA2 and EDG-7/LPA3 are consistently up-regulated in malignant ovarian epithelial cells contributing to the aberrant response of ovarian cancer cells to LPA. These receptors kick off signalling through the $G_i$, the $G_{q,11}$, or the $G_{12,13}$ pathways in the cell. Alteration of the signalling through these pathways is common to all drugs targeting GPCRs, which account for more than half of the marketed drugs today in various indications.

High levels of LPA are generated during blood coagulation due to the release of phospholipase PLA1 and sPLA2 from platelets that convert phosphatidic acid to LPA. LPA is considered to be one of the most potent growth factors in serum used for the growth of cells in vitro.

DESCRIPTION OF THE INVENTION

It is the object of the present invention to provide novel LPA receptor antagonists useful in the treatment of proliferative or inflammatory diseases, especially those related to the hyperactivity of LPA, such as cancer, fibrosis or arthritis, in mammals, with superior pharmacological properties both with respect to their activities as well as their solubility, metabolic clearance and bioavailability characteristics.

As a result, this invention provides novel substituted benzyl piperidine compounds or their stereoisomers or tautomers, or pharmaceutically acceptable salts, that are LPA antagonists and useful as medicaments, especially in the treatment of the above mentioned diseases.

The compounds are defined by Formula (I):

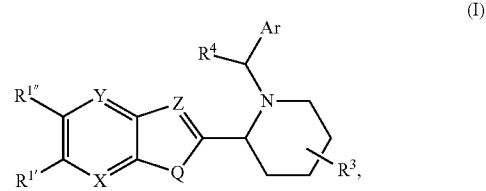

wherein:
$R^{1'}$, $R^{1''}$, $R^2$, $R^3$, $R^4$, $R^{5'}$, $R^{5''}$ are independently H, Hal, OH, CN, $NO_2$, $NH_2$, A, NH(LA), $N(LA)_2$, COOH, COO(LA), $SO_2(LA)$, O(LA), $SO_2NH_2$, $SO_2NH(LA)$, $SO_2N(LA)_2$,
X, Y, Z are independently CH, C(LA), C(Hal) or N,
Q is $NR^2$, O or S,
LA is unbranched or branched alkyl having 1, 2, 3 or 4 carbon atoms, wherein one, two or three H atoms may be replaced by Hal,
$R^3$ is H or LA,
Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, or disubstituted by $R^{5'}$, $R^{5''}$,
Hal is F, Cl, Br or I.

In general, all residues which occur more than once may be identical or different, i.e. are independent of one another. Above and below, the residues and parameters have the meanings indicated for the Formula (I), unless expressly indicated otherwise. Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine.

"LA" denotes unbranched or branched, linear alkyl having 1, 2, 3 or 4 C atoms, wherein 1, 2 or 3 H atoms may be replaced by Hal, e.g. methyl, ethyl, trifluoromethyl, difluoromethyl, 1,1,1-trifluoroethyl, propyl, isopropyl, butyl, isobutyl, sec-butyl or tert-butyl.

"Ar" denotes, for example, unsubstituted phenyl, or naphthyl, furthermore preferably, for example, phenyl or naphthyl, each of which is mono-, or disubstituted by methyl, ethyl, isopropyl, fluorine, chlorine, bromine, hydroxyl, methoxy, ethoxy, propoxy, nitro, cyano, formyl, acetyl, propionyl, trifluoromethyl, methanesulfonyl, amino, methylamino, dimethylamino, diethylamino, carboxyl, methoxycarbonyl.

"Ar" furthermore denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methyl-amino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methyl-sulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, p-iodophenyl, 4-fluoro-3-chlorophenyl, 2-fluoro-4-bromophenyl, 3-bromo-6-methoxyphenyl, 3-chloro-6-methoxyphenyl, 3-fluoro-4-methoxyphenyl, 3-amino-6-methylphenyl.

"Ar" furthermore preferably denotes 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4-, 5-, 6- or 7-indazolyl, 2-, 3-, 4- or 5-isoindolyl, 2-, 6, -or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, each of which is unsubstituted, or mono-, or disubstituted by methyl, ethyl, isopropyl, fluorine, chlorine, bromine, hydroxyl, methoxy, ethoxy, propoxy, nitro, cyano, formyl, acetyl, propionyl, trifluoromethyl, methanesulfonyl, amino, methylamino, dimethylamino, diethylamino, carboxyl, methoxycarbonyl.

The compound 3-ethyl-2-1[-(phenylmethyl)-2-piperidinyl]-1H-indole is known from patent document FR70999 (CAS registry number 106545-83-9) and is, therefore, excluded from the claims of this patent application.

In a preferred embodiment of Formula (I) the stereochemistry at the chiral carbon atom of the piperidine ring is as shown in Formula (I'):

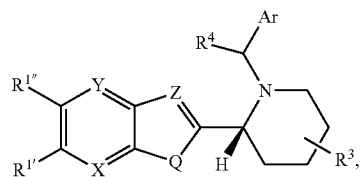

wherein all residues have the meaning indicated for Formula (I).

Further preferred are compounds of Subformulae 1 to 19 of Formulae (I) and (I'), wherein
in Subformula 1
$R^{1'}$, $R^{1'''}$ are independently H, methyl, F, Cl, Br or $SO_2NH_2$,
in Subformula 2
$R^4$ is H or methyl,
in Subformula 3
$R^3$ is H or methyl,
in Subformula 4
Ar is phenyl, furyl, pyridyl, thiazolyl or indazolyl,
in Subformula 5
$R^{5'}$, $R^{5'''}$ are independently H, F, methyl, ethyl, methoxy, trifluoromethyl, hydroxy or nitro,
in Subformula 6
$R^{1'}$, $R^{1'''}$ are independently H, methyl, F, Cl, Br or $SO_2NH_2$,
$R^3$ is H or methyl,
$R^4$ is H or methyl,
Ar is phenyl, furyl, pyridyl, thiazolyl or indazolyl,
$R^{5'}$, $R^{5'''}$ are independently H, F, methyl, ethyl, methoxy, trifluoromethyl, hydroxy or nitro,
in Subformula 7
$R^3$ is H,
in Subformula 8
$R^4$ is H,
in Subformula 9
Ar is phenyl,
in Subformula 10
Q is $NR^2$,
$R^2$ is H, methyl or isopropyl,
Z is N,
in Subformula 11
Q is $NR^2$,
$R^2$ is H, methyl or isopropyl,
Z is CH,
in Subformula 12
Y is CH, C(LA) or C(Hal),
X is N,
in Subformula 13
Y is CH, C(LA) or C(Hal),
X is CH,
in Subformula 14
Y is CH, C—$CH_3$ or C—F,
X is N,
in Subformula 15
Y is CH, C—$CH_3$ or C—F,
X is CH,
in Subformula 16
Q is NH,
Z is CH,
$R^1$ is H,
$R^{1'''}$ is F,
in Subformula 17
Q is NH,
Y is CH, in Subformula 18
Ar is phenyl,
$R^{5'}$, $R^{5''}$ are independently H, F or methyl,
in Subformula 19
$R^3$ is H,
$R^4$ is H,
Ar is phenyl,
$R^{5'}$, $R^{5''}$ are independently H, F or methyl,
Q is NH,
Y is CH,
and the remaining residues have the meaning as indicated for Formula (I).

The compounds of the Formula (I) may have one or more centres of chirality. They may accordingly occur in various enantiomeric forms and be in racemic or optically active form. The invention, therefore, also relates to the optically active forms, enantiomers, racemates, diastereomers, collectively: stereoisomers, of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like.

If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable solvates" means addition forms with pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

Therefore, the following items are also in accordance with the invention:
  a) all stereoisomers or tautomers of the compounds, including mixtures thereof in all ratios,
  b) prodrugs of the compounds, or stereoisomers or tautomers of these prodrugs,
  c) pharmaceutically acceptable salts of the compounds and of the items mentioned under (a) and (b),
  d) pharmaceutically acceptable solvates of the compounds and of the items mentioned under (a), (b) and (c).

It should be understood that all references to compounds above and below are meant to include these items, in particular pharmaceutically acceptable solvates of the compounds, or pharmaceutically acceptable solvates of their pharmaceutically acceptable salts.

The invention also relates to the use of a compound according to the invention for the preparation of a medicament for the treatment of proliferative or inflammatory diseases related to the hyperactivity of LPA as well as diseases modulated by LPA in mammals, or disorders mediated by aberrant proliferation, such as cancer.

This invention also relates to a compound or pharmaceutical composition for inhibiting abnormal cell growth in a mammal which comprises an amount of a compound of the present invention, in combination with an amount of another anti-cancer therapeutic, wherein the amounts of the compound, and of the other anti-cancer therapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, integrin antagonists, such as cilengitide, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of a protein kinase, auch as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a proliferative disorder that comprises administering to the mammal an amount of a compound of the present invention or pharmaceutical composition, in combination with radiation therapy, wherein the amounts of the compound or pharmaceutical composition, is in combination with the radiation therapy effective in inhibiting abnormal cell growth or treating the proliferative disorder in the mammal. Techniques for administering radiation therapy are known in the art, and these techniques can be used in the combination therapy described herein. The administration of a compound of the invention, or pharmaceutical composition, in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutical composition, which amount is effective in sensitizing abnormal cells to treatment with radiation. The amount of the compound in this method can be determined according to the means for ascertaining effective amounts of such compounds described herein.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray. The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or its stereoisomers or tautomers, or pharmaceutically acceptable salts of each of the foregoing, including mixtures thereof in all ratios, and
b) an effective amount of a further medicament active ingredient.

The set comprises suitable containers, such as boxes, individual bottles, bags or ampoules.

By way of example, the set may comprise separate ampoules, each containing an effective amount of a compound according to the invention, and an effective amount of a further medicament active ingredient in dissolved or lyophilised form.

Experimental Section

Some abbreviations that may appear in this application are as follows:

| Abbreviations | |
|---|---|
| Designation | |
| ACN | acetonitrile |
| ATP | Adenosine triphosphate |
| b | Broad peak |
| d | Doublet |
| DMSO | dimethylsulfoxide |
| DTT | dithiothreitol |
| EDTA | Ethylenediaminetetraacetic acid |
| equiv. | equivalents |
| Et | ethyl |
| h | hour |
| HEPES | 4-(2-hydroxyethyl)-1-piperazineethanesulfonic acid |
| HPLC | High Pressure Liquid Chromatography |
| LC/MS | Liquid Chromatography coupled to Mass Spectrometry |
| m | multiplet |
| M | Molecular ion |
| m/z | Mass-to-charge ratio |
| Me | methyl |
| min | minute |
| MS | Mass spectrometry |
| N | Normal (unit of concentration) |
| NMR | Nuclear Magnetic Resonance |
| PG | Protecting group |
| psi | Pounds per square inch |
| q | Quartette (or quartet) |
| Rf | Retention factor |
| RT | Room temperature |
| Rt. | Retention time |
| s | Singlet |
| Tert | Tertiary |
| TFA | Trifluoroacetic Acid |
| THF | Tetrahydrofuran |
| UV | ultraviolet |
| VIS | visible |
| DMEM | Dulbecco's Modified Eagle's Medium |
| FCS | Fetal Calf Serum |
| PBS | Phosphate Buffered Saline |
| HBBS | Hank's Balanced Salt Solution |
| BSA | Bovine Serum Albumin |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at room temperature. Compounds were purified by either silica chromatography or preparative HPLC.

The present invention relates also to a process for the manufacture of compounds of Formula (I), wherein a compound of Formula (III)

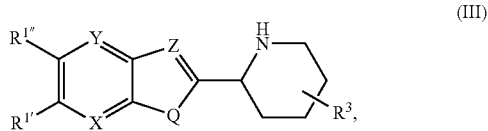

is reacted with a compound of Formula (II)

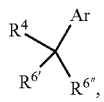

via amination, wherein $R^{6'}$ is a leaving group and $R^{6''}$ is H, or $R^{6'}$ and $R^{6''}$ together form a leaving group, to yield a compound of Formula (I).

Where the amination reaction is nucleophilic substitution, preferably $R^{6'}$ is Hal, such as Cl or Br. Where the amination reaction is reductive amination, $R^{6'}$ and $R^{6''}$ together form a leaving group, which is preferably carbonyl oxygen.

EXAMPLES

The working examples presented below are intended to illustrate particular embodiments of the invention, and are not intended to limit the scope of the specification or the claims in any way.

Chemical Synthesis

In this section experimental details are provided for a number of representative Example compounds according to Formula (I), and synthesis intermediates thereof.

Synthesis of 2-[1-(3-Methyl-benzyl)-piperidin-2-yl]-1H-indole

Example Compound 2

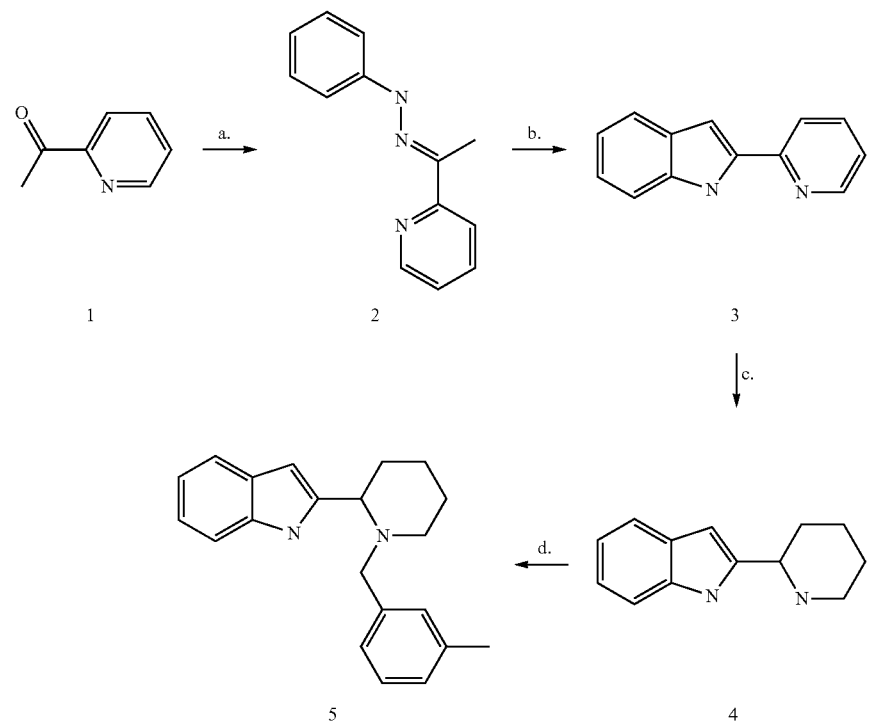

a. 2-acetylpyridine 1 (5.99 g, 40.9 mmol) was dissolved in absolute ethanol (50 mL), phenylhydrazine (8.85 g, 81.8 mmol) was added and the solution was refluxed for 30 min. After cooling to room temperature the precipitate obtained was collected by filtration, washed with cold ethanol and dried under reduced pressure. The off-white solid was identified as compound 2 in a yield of 92.4% (8.67 g, 37.8 mmol) and was used without further purification.

b. The hydrazone 2 (7.74 g, 36.6 mmol) was mixed with polyphosphoric acid (43.5 g) in a heavy-walled beaker and heated at 110° C. for 1.5 h. After cooling, the mixture was basified with 10% NaOH and extracted with dichloromethane. The combined organic extracts were dried over sodium sulphate, filtered and evaporated to dryness. The residue was purified by flash chromatographt on silica gel using hexane:dichloromethane 1:1 as eluent system to yield in a colorless solid identified as compound 3 (5.31 g, 27.3 mmol, 75%).

c. Compound 3 (5.16 g, 26.6 mmol) was dissolved in absolute methanol (100 mL), 0.2 ml acetic acid and 10% Pd/C were added. The mixture was hydrogenated in an autoclave under $H_2$ (80 atm) at 50°. After 12 h of stirring 1 g Pd/C and 0.2 ml acetic acid was added additionally and the mixture was hydrogenated for 12 h under $H_2$ (80 atm) at 50° C.. After cooling the reaction mixture was filtered through Celite and concentrated under reduced pressure. The crude product was purified by flash chromatography on silica gel (hexane:dichloromethane 1:1) followed by crystallization from ethyl ether. Compound 4 was obtained as colorless solid (5.14 g, 25.7 mmol, 96%).

d. To the solution of compound 4 (200 mg, 1.00 mmol) in dichloromethane (5 mL), 3-Methylbenzaldehyde (120 mg, 1.00 mmol) was added to RT and stirring was continued for 15 min. To this solution sodium triacetoxyborhydride (300 mg, 1.42 mmol) was added at RT and stirring was continued for 12 h. Water was added to the reaction and the aqueous layer was extracted with dichloromethane. The organic layer was dried over sodium sulphate, filtered and concentrated under reduced pressure. The pure product was isolated by flash chromatography using dichloromethane:methanol as eluent system with gradient of methanol from 0% to 0.5%. Final compound 5 was obtained as colorless solid (228 mg, 0.75 mmol, 75%).

Alternative procedure: To the solution of compound 4 (100 mg, 0.50 mmol) in acetonitrile (5 mL), potassium carbonate (69.1 mg, 0.50 mmol) and 3-methylbenzyl bromide (92.5 mg, 0.50 mmol) was added at RT and stirring was continued at 80° C. for 15 h. Water and ethyl acetate were added to the reaction and the aqueous layer was separated and extracted twice with ethyl acetate. The combined organic layer were dried over sodium sulphate, filtered and concentrated under reduced pressure. The pure product was isolated by flash chromatography (dichloromethane:methanol). Final compound 5 was obtained as colorless solid (82.6 mg, 0.24 mmol, 48%). According to this procedure the following Example compounds were synthesized, as shown in Table 1: 1-10, 13-25, 42-44, 54-60, 63, 65-71, 73, 82, 84-86, 107-112, 124, 125, 132, 136-139 and 143.

Example 72 compound was prepared by reacting the corresponding piperidine derivative with 1-(4-Fluorophenyl)-ethanone in analogy to procedure d.

To synthesize Example compound 75 instead of 2-acetylpyridine 1-pyridine-2-yl-propan-1-one was used in procedure a. The following steps were performed according to procedures b-d.

Synthesis of 5-Fluoro-2-[1-(4-fluoro-benzyl)-6-methyl-piperidin-2-yl]-1H-indole

Example Compound 36

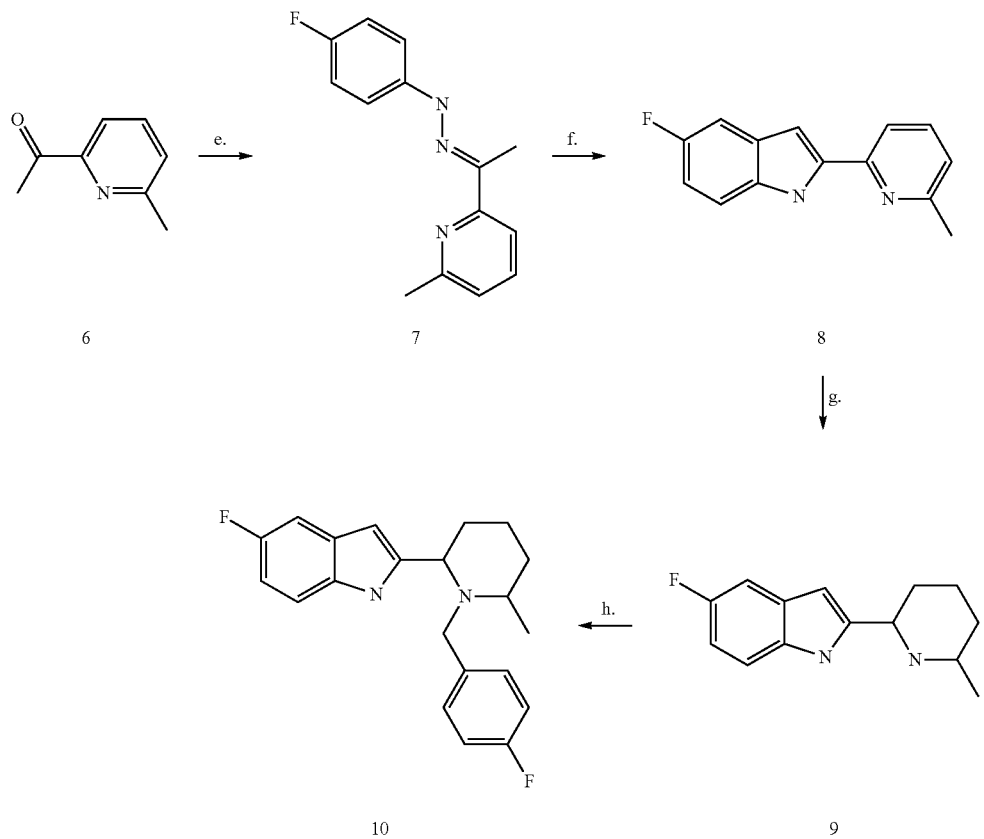

e. 2-acetyl-6-methylpyridine 6 (10.0 g, 99%, 73.2 mmol) was dissolved in absolute ethanol (100 mL), 4-Fluoro-phenylhydrazine (25.1 g, 95%, 147 mmol) was added and the solution was refluxed for 30 min. After cooling to room temperature the precipitate obtained was collected by filtration, washed with cold ethanol. The residue was redissolved in saturated sodium carbonate solution and extraced with dichloromethane twice. The combined organic layers were dried over sodium sulphate, filtered and evaporated to dryness under reduced pressure. The off-white solid was identified as compound 7 in a yield of 92.5% (16.5 g, 67.8 mmol) and was used without further purification.

f. The hydrazone 7 (16.5 g, 67.5 mmol) was mixed with polyphosphoric acid (42.0 g, 99%, 424 mmol) in a heavy-walled beaker and heated at 110° C. for 1.5 h. After cooling, the mixture was basified with 10% NaOH and extracted with dichloromethane. The combined organic extracts were dried over sodium sulphate, filtered and evaporated to dryness. The residue was purified by flash chromatography on silica gel using hexane:dichloromethane 3:2 as eluent system to yield in a colorless solid identified as compound 8 (5.62 g, 95%, 24.8 mmol, 37%).

g. Compound 8 (1.59 g, 95%, 6.68 mmol) was dissolved in absolute methanol (25 mL), 0.2 ml acetic acid and 10% Pd/C were added. The mixture was hydrogenated in an autoclave under $H_2$ (76 atm) at 50° C for 12 h. After cooling the reaction mixture was filtered through Celite and concentrated under reduced pressure. The crude product was purified by flash chromatography on silica gel (hexane:dichloromethane 1:1) followed by crystallization from ethyl ether. Compound 9 was obtained as colorless solid (0.77 g, 3.31 mmol, 50%).

h. To the solution of compound 9 (105 mg, 0.45 mmol) in dichloromethane (4 mL), 4-Flouorobenzaldehyde (71 mg, 95%, 0.54 mmol) was added at RT and stirring was continued for 15 min. To this solution sodium triacetoxyborhydride (300 mg, 1.42 mmol) was added at RT and stirring was continued for 12 h. at 50° C.. Additionally 1.2 eq of aldehyde and 2 eq of NaBH(OAc)₃ was added and reaction mixture was stirred for 3 h at RT and then stirred for 3 days at 50° C. Water was added to the reaction and the aqueous layer was extracted with dichloromethane. The organic layer was dried over sodium sulphate, filtered and concentrated under reduced pressure. The pure product was isolated by flash chromatography using dichloromethane:methanol as eluent system with gradient of methanol from 0% to 0.5%. Final compound 10 was obtained as colorless solid (72 mg, 0.21 mmol, 47%).

According to this procedure the following Example compounds were synthesized, as shown in Table 1, starting with 2-acetyl-5-methylpyridine, 2-acetyl-4-methylpyridine and 2-acetyl-3-methylpyridine: Examples 26-41, 45, 46, 61, 62, 64, 68, 74, 76, 79-81, 83, 87.

6-Chloro-2-[1-(3,4-dimethyl-benzyl)-piperidin-2-yl]-3H-imidazo[4,5-b]pyridine

Example Compound 128

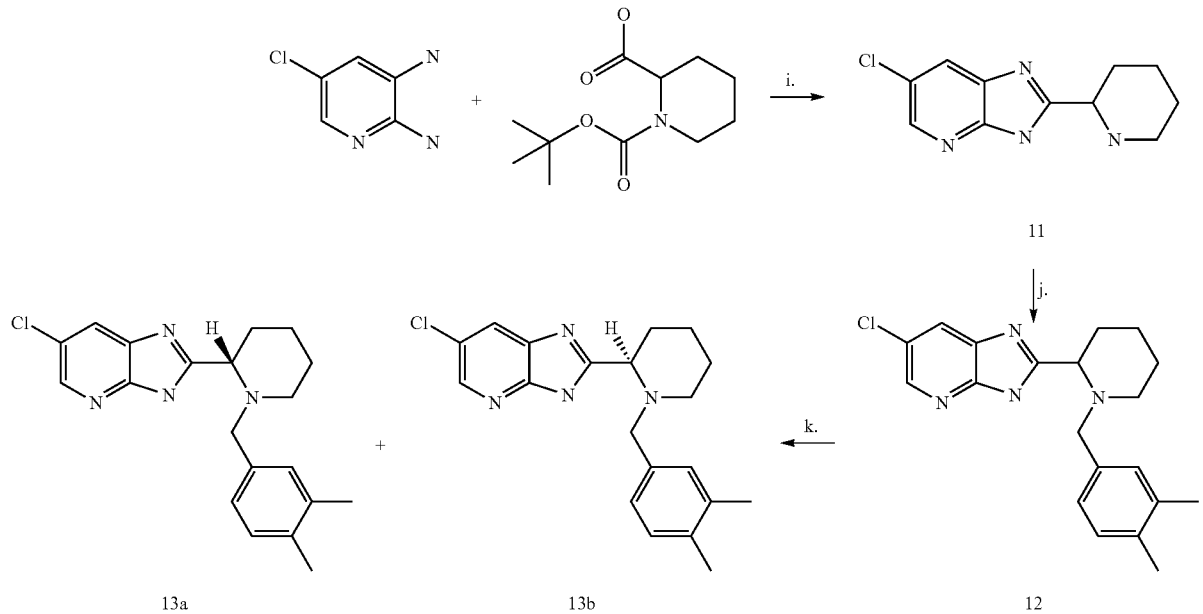

i. 5-Chloro-2,3-diaminopyridine (300 mg, 98%, 2.05 mmol) and 1-tert. Butoxycarbonylpiperidine-2-carboxylic acid (540 mg, 2.36 mmol) was dissolved in Polyphosphoric acid (1.5 mL) and stirred 18 h at 160° C.. The mixture was poured on ice and extracted with Ethyl acetate/butanol twice. The combined organic layer was dried with MgSO4, filtered and evaporated to dryness. The residue was identified as compound 11 and was used without further purification (462 mg, 1.95 mmol, 95%).

j. To the solution of compound 11 (100 mg, 0.42 mmol) in N,N-Dimethylformamide (2 mL), potassium carbonate (70 mg, 0.51 mmol) and 3,4-Dimethylbenzylic chloride (95 mg, 70% purity, 0.43 mmol) was added at RT and stirring was continued at RT for 15 h. Water and ethyl acetate were added to the reaction and the aqueous layer was separated and extracted twice with ethyl acetate. The combined organic layers were dried over sodium sulphate, filtered and concentrated under reduced pressure. The pure product was isolated by flash chromatography (dichloromethane:methanol). Final compound 12 was obtained as colorless solid (85.0 mg, 0.24 mmol, 57%).

k. Compound 12 (50 mg) was dissolved in ethanol (5 mL) and separated by chiral HPLC using a 5 × 50 cm Chiralpak AD-column with 20 μm material with a flow rate of 120 mL/min with the solvent n-heptan/ethanol 70/30 into the enantiomeres (see Examples 140, 141 in Table 1). 18.1 mg of 13a and 19,3 of 13b were obtained.

According to this procedure the following Example compounds were synthesized, as shown in Table 1, also using 2,3-Diaminopyrazine: Examples 128, 130, 133, 134, 144.

Synthesis of 6-Chloro-5-methyl-2-[1-(3-methyl-benzyl)-piperidin-2-yl]-1H-benzoimidazole Example Compound 106

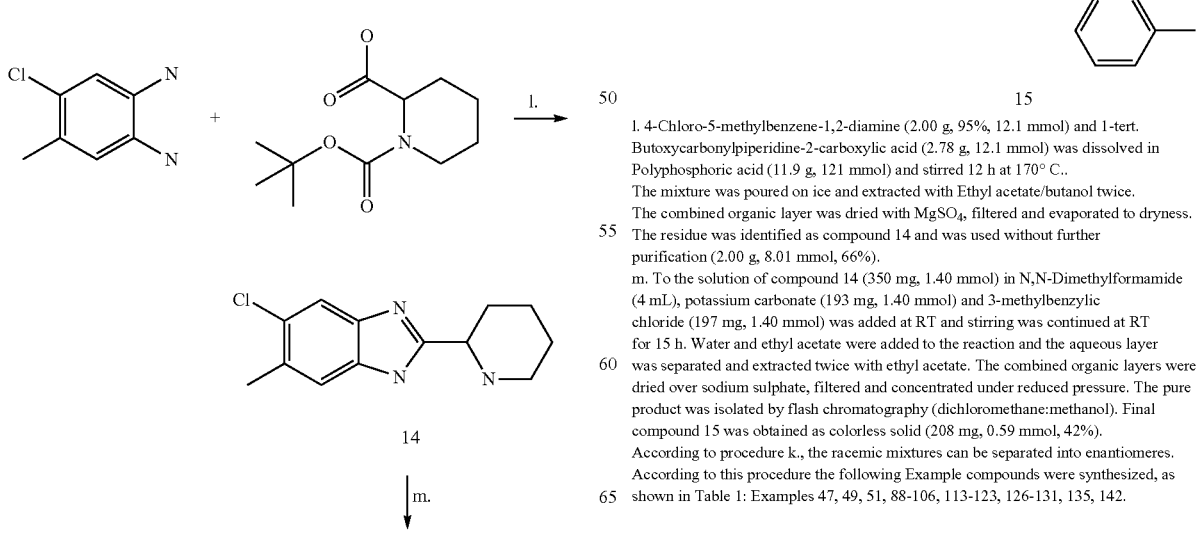

l. 4-Chloro-5-methylbenzene-1,2-diamine (2.00 g, 95%, 12.1 mmol) and 1-tert. Butoxycarbonylpiperidine-2-carboxylic acid (2.78 g, 12.1 mmol) was dissolved in Polyphosphoric acid (11.9 g, 121 mmol) and stirred 12 h at 170° C.. The mixture was poured on ice and extracted with Ethyl acetate/butanol twice. The combined organic layer was dried with MgSO4, filtered and evaporated to dryness. The residue was identified as compound 14 and was used without further purification (2.00 g, 8.01 mmol, 66%).

m. To the solution of compound 14 (350 mg, 1.40 mmol) in N,N-Dimethylformamide (4 mL), potassium carbonate (193 mg, 1.40 mmol) and 3-methylbenzylic chloride (197 mg, 1.40 mmol) was added at RT and stirring was continued at RT for 15 h. Water and ethyl acetate were added to the reaction and the aqueous layer was separated and extracted twice with ethyl acetate. The combined organic layers were dried over sodium sulphate, filtered and concentrated under reduced pressure. The pure product was isolated by flash chromatography (dichloromethane:methanol). Final compound 15 was obtained as colorless solid (208 mg, 0.59 mmol, 42%).

According to procedure k., the racemic mixtures can be separated into enantiomeres.

According to this procedure the following Example compounds were synthesized, as shown in Table 1: Examples 47, 49, 51, 88-106, 113-123, 126-131, 135, 142.

Synthesis of 2-[1-(4-Fluoro-benzyl)-piperidin-2-yl]-1H-pyrrolo[2,3-b]pyridine

Example Compound 144

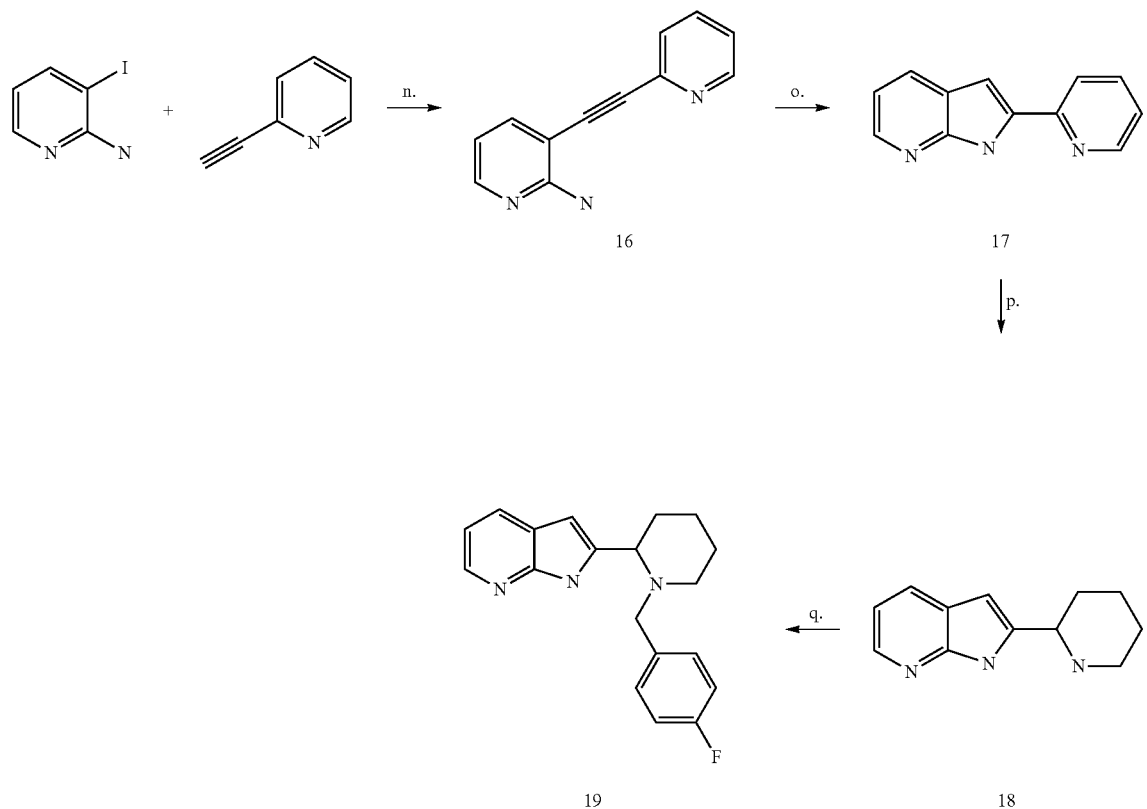

n. 3-Iodo2-aminopyridine (1.00 g, 99%, 4.54 mmol), lithium chloride (289 mg, 6.81 mmol) and sodium carbonate (1.93 g, 18.2 mmol) were dried 1 h in a vacuum oven at 100° C.. The Reaction vessel was spilled with Argon and cooled to RT. To the mixture dry degassed N,N-dimethylformamide (25 mL), 2-ethynylpyridine (563 mg, 5.45 mmol) and the catalyst Pd(dppf)Cl2*CH2Cl2 (371 mg, 0.54 mmol) were added and stirring was continued for 18 h at 100° C.. After cooling to RT water was added and the mixture was extracted with ethyl acetate twice. The combined organic layers were dried over sodium sulphate, filtered and the solvent was evaporated to dryness in vacuo. The residue was purified by flash chromatography on silica gel using a gradient from cyclohexane:ethyl acetate 1:1 to 100% ethyl acetate as eluent system to yield in a colorless solid identified as compound 16 (555 mg, 2.85 mmol, 63%).

o. Compound 16 (545 mg, 2.79 mmol) was dissolved in dry THF (25 mL) and sodium hydride (60% in mineral oil, 366 mg, 9.20 mmol, washed twice with dry hexane) was added in small portions over 5 min. the misture was stirred for 2 d at 80° C.) in a sealed vessel. The mixture was poured onto ice and extracted 3 times with ethyl acetate, The combined organic extracts were dried over sodium sulphate, filtered and evaporated to dryness. The residue was purified by flash chromatography on silica gel using a gradient from cyclohexane:ethyl acetate 1:1 to 100% ethyl acetate as eluent system to yield in a colorless solid identified as compound 17 (311 mg, 1.59 mmol, 57%).

p. Compound 17 (311 mg, 1.59 mmol) was dissolved in absolute methanol/acetic acid (10 mL, 1:1) and 10% Pd/C (0.30 g) were added. The mixture was hydrogenated in an autoclave under $H_2$ (1 atm) at RT. After 18 h of stirring 1 g Pd/C was added additionally and the mixture was hydrogenated for additional 40 h at RT. After cooling the reaction mixture was filtered through Celite and concentrated under reduced pressure. The crude product was purified by flash chromatography on silica gel (dichloromethane:methanol). Compound 18 was obtained as colorless solid (92.1 mg, 0.46 mmol, 29%).

q. To the solution of compound 18 (46.0 mg, 0.23 mmol) in acetonitrile (2.5 mL), potassium carbonate (31.6 mg, 0.23 mmol) and 4-Fluorobenzyl bromide (43.5 mg, 0.23 mmol) was added at RT and stirring was continued at 80° C. for 15 h. Water and ethyl acetate were added to the reaction and the aqueous layer was separated and extracted twice with ethyl acetate. The combined organic layer were dried over sodium sulphate, filtered and concentrated under reduced pressure. The pure product was isolated by flash chromatography (dichloromethane:methanol). Final compound 19 was obtained as colorless solid (21.8 mg, 0.07 mmol, 31%).

Synthesis of 2-[1-(3,4-Dimethyl-benzyl)-4-isopropyl-piperazin-2-yl]-1H-benzoimidazole Example Compound 53

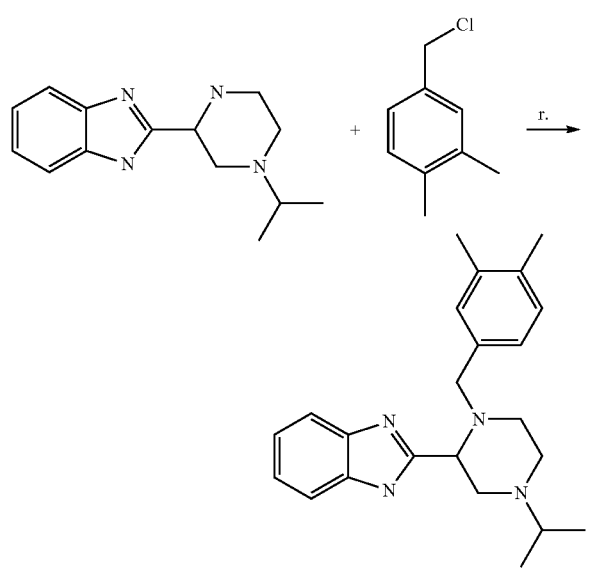

r. To the commercially available 2-(4-Isopropyl-piperazin-2-yl)-1H-benzoimidazole (14.7 mg, 0.06 mmol) in acetonitrile (2.5 mL), potassium carbonate (9 mg, 0.06 mmol) and 3,4-dimethylbenzyl chloride (13.9 mg, 70%, 0.06 mmol) was added at RT and stirring was continued at RT for 15 h. Water and ethyl acetate were added to the reaction and the aqueous layer was separated and extracted twice with ethyl acetate. The combined organic layer were dried over sodium sulphate, filtered and concentrated under reduced pressure. The pure product was isolated by flash chromatography (ethyl acetate:methanol). Final compound 20 was obtained as colorless solid (7.8 mg, 0.02 mmol, 36%).
According to this procedure, also commericaly available 2-Benzofuran-2-yl-piperidine can be reacted to Example compounds 48 and 50, 2-Piperidin-2-yl-benzothiazole to Example compound 52.

Biological Activity
1. Biochemical Enzyme Assay for LPA Activity

The assay detects intra cellular calcium which is generated by cells upon activation of the LPA2 receptor by its ligand LPA. This transient calcium mobilization can be monitored using a commercial calcium detection kit (e.g. from Molecular Devices). The main component of such a kit is a dye, which becomes fluorescent when calcium is present—a transient fluorescence signal after laddition of a ligand to a test well are the result. Readers like the FLIPR (Molecular Devices) can be used to monitor such transient "Ca-flux" signals.

The signals are calculated according to peak maximum minus base line.

Compounds which are antagonists of LPA lead to a decreased mobilisation of intracellular calcium and thus to a lower signal. The assay is performed in microplates (384 wells per plate).

Reagents
Cell Culture

| cell line | U2OS, recombinant expressing LPA2R |
| --- | --- |
| McCoy's Medium | Invitrogen #26600-021 |
| DMEM | Gibco #41965 |
| Penicillin/Streptomycin | Gibco #15140 |
| FCS | PAA #A15-043 |
| Geniticin | Invitrogen #10131-027 |
| PBS | Gibco |
| HEPES | Gibco #15630-056 |
| HyQ-Tase | HyClone #SV30030.01 |

Assay

| 10 × HBSS | Gibco #14065 |
| --- | --- |
| 1M HEPES | Merck #1.10110 |
| NaCl | Merck #1.06404 |
| KCl | Merck #1.04936 |
| $MgSO_4 \times 7H_2O$ | Merck #1.05886 |
| $CaCl_2 \times 2H_2O$ | Merck #1.02382 |
| D(+)-Glucose × $1H_2O$ | Merck #1.04074 |
| BSA, fatty acid free | Roche #10 77 58 35 001 |
| ligand (LPA), 1-Oleoyl-2-Hydroxy-sn-Glycero-3-Phosphate, | Invitrogen #P36400 Avanti #857130P |
| probenecid, water soluble | |
| detection solution (calcium dye) | Bulk Kit (Molecular Devices #R8141) |
| micro plate 384 blck, cl.bottom | Falcon #353692 |

Cell Cultivation/Propagation

| medium | McCoy's Medium, 10% FCS, 1 mg/ml Geniticin |
| --- | --- |
| culture conditions | 37° C., 5% $CO_2$ in T75 flasks |
| harvesting | washing with PBS |
| | detaching with 1 mL HyQ-Tase per flask |
| | incubation 5 min |
| | addition of 10 mL medium |
| | centrifugation |
| | re-suspension with 10 mL culture medium |

LPA2R-Calciumflux Assay Protocol
The assay is run according to the following procedure:
50 uL seed cells (10000 cells/well in DMEM buffer)
  Incubate 24 h at 37° C., 10% $CO_2$
  aspirate medium
50 uL add calcium dye 1×HBSS/HEPES buffer
  incubate 1 h at 37° C. ("loading")
  equilibrate 10 min at RT
5 uL add compounds in HEPES buffer
  shake 10 sec. at 1000 rpm
  incubate 15 min at RT
20 uL add LPA (in the FLIPR Tetra) in Krebs-buffer/BSA & measurement The cells are seeded in DMEM buffer (DMEM, 10% FCS, 10 mM HEPES, 1% Pen/Strep).

Dye loading is done in HBSS/HEPES buffer (100 mL 10×HBSS+20 mL 1M HEPES+880 mL water, pH 7.4)

The LPA is added in Krebs/BSA buffer (120 mM NaCl, 5 mM KCl, 0.62 mM $MgSO_4$, 1.8 mM $CaCl_2$, 10 mM HEPES, 6 mM D(+)-Glucose, 0.2% BSA, pH 7.4).

The compounds are pre-diluted in HEPES buffer (20 mM, pH 7.4), whereby the final DMSO content in the assay is kept at 1%. The compounds are pre-diluted in order to generate dose response series on the microplates. The dose response series consist of 10 concentrations for each compound from 30 uM final to 1 nM final. From all compound wells the resulting signals are referred to control wells (located on each plate besides the compound wells) in terms of % activity.

$$\% \text{ activity} = \frac{(\text{readout}_{compoupd} - \text{readout}_{blank})}{(\text{readout}_{full} - \text{readout}_{blank})} * 100$$

From these % activity values—along with the corresponding compound concentrations—IC50 values are fitted for each compound using standard fitting programs such as Graphpad Prism. Here the method "log(inhibitor) vs. response—Variable slope" is used.

Reader Settings (FLIPR Tetra)
ExcWLength: 470_495
Em.Wlength: 515_575
Gain: 50
Exp. Time: 0,4
Exc.Intensity: 80
READ with TF
First read interval: 1.00 s
Number of first reads: 240
Reads before dispense: 10
Second read interval: 1.00 s
Number of second reads: 0
Save Images: No To assess the inhibitory potential of the compounds on LPA2R, $IC_{50}$-values were determined, as shown in Table 1 below, whereby the following classification is used:

TABLE 1

| Example Compound[4] | Chemical Structure | MW [g/mol] | $[M + 1]^+$ | HPLC Rt $[min]^{1,2,3}$ | IC50 [μM] | Chemical Name | NMR |
|---|---|---|---|---|---|---|---|
| 1 | 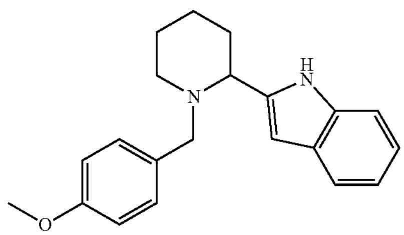 [SMILES: COc1ccc(CN2CCCCC2c2cc3ccccc3[nH]2)cc1] | 320.43 | 321 | 3.49[3] | +++ | 2-[1-(4-Methoxy-benzyl)-piperidin-2-yl]-1H-indole | |
| 2 | 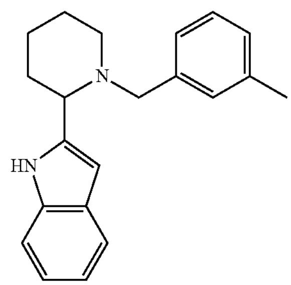 [SMILES: Cc1cccc(CN2CCCCC2c2cc3ccccc3[nH]2)c1] | 304.43 | 305 | 3.73[3] | ++++ | 2-[1-(3-Methyl-benzyl)-piperidin-2-yl]-1H-indole | 1H NMR (400 MHz, DMSO) δ 11.07 (s, 1H), 7.44 (d, J = 7.7, 1H), 7.36 (d, J = 7.7, 1H), 7.22-7.11 (m, 1H), 7.11-7.03 (m, 2H), 7.03-6.97 (m, 2H), 6.95-6.90 (m, 1H), 6.35 (d, J = 1.4, 1H), 3.61 (d, J = 13.3, 2H), 3.17 (s, 1H), 2.87-2.80 (m, 2H), 2.26 (s, 3H), 1.99-1.89 (m, 1H), 1.86-1.74 (m, 2H), 1.64-1.29 (m, 3H). |
| 3 | 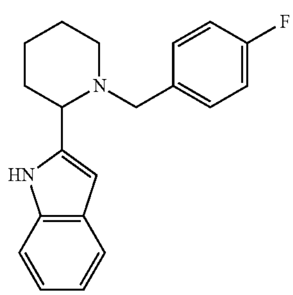 [SMILES: Fc1ccc(CN2CCCCC2c2cc3ccccc3[nH]2)cc1] | 308.40 | 309 | 3.51[3] | ++++ | 2-[1-(4-Fluoro-benzyl)-piperidin-2-yl]-1H-indole | $^1$H NMR (400 MHz, DMSO) δ 11.10 (s, 1H), 7.44 (d, J = 7.6 Hz, 1H), 7.38-7.28 (m, 3H), 7.17-7.05 (m, 2H), 7.01 (t, J = 7.2 Hz, 1H), 6.91 (t, J = 7.2 Hz, 1H), 6.35 (s, 1H), 3.58 (d, J = 13, 1H), 3.17 (d, J = 4.9 Hz, 1H), 2.90 (d, J = 13.4 Hz, 1H), 2.80 (d, J = 11.4 Hz, 1H), 2.01-189 (m, 1H), 1.88-1.75 (m, 3H), 1.66-1.28 (m, 3H). |
| 4 | 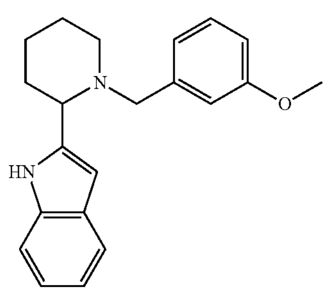 [SMILES: COc1cccc(CN2CCCCC2c2cc3ccccc3[nH]2)c1] | 320.43 | 321 | 3.52[3] | ++++ | 2-[1-(3-Methoxy-benzyl)-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 5 | 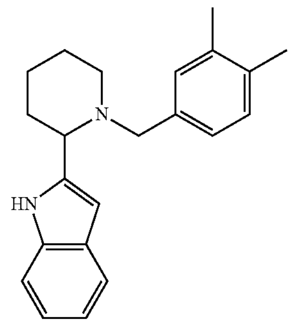 [SMILES: Cc1ccc(CN2CCCCC2c2cc3ccccc3[nH]2)cc1C] | 318.46 | 319 | 3.97[3] | ++++ | 2-[1-(3,4-Dimethyl-benzyl)-piperidin-2-yl]-1H-indole | |
| 6 | 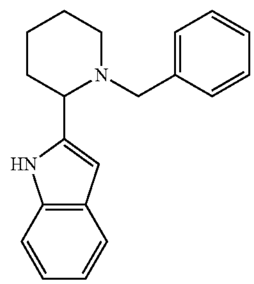 [SMILES: c1ccc(CN2CCCCC2c2cc3ccccc3[nH]2)cc1] | 290.41 | 291 | 3.39[3] | +++ | 2-(1-Benzyl-piperidin-2-yl)-1H-indole | |
| 7 | 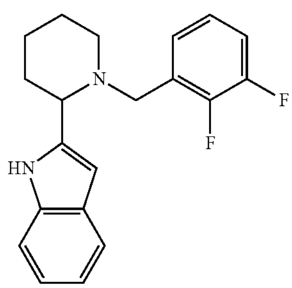 [SMILES: Fc1cccc(CN2CCCCC2c2cc3ccccc3[nH]2)c1F] | 326.39 | 327 | 3.40[3] | +++ | 2-[1-(2,3-Difluoro-benzyl)-piperidin-2-yl]-1H-indole | |
| 8 | 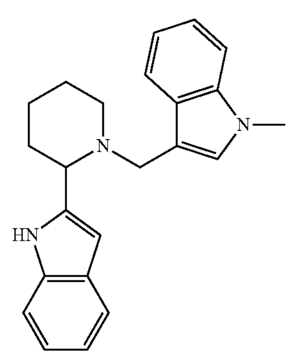 [SMILES: Cn1cc(CN2CCCCC2c2cc3ccccc3[nH]2)c2ccccc21] | 343.47 | 344 | 3.86[3] | +++ | 3-[2-(1H-Indol-2-yl)-piperidin-1-ylmethyl]-1-methyl-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 9 | 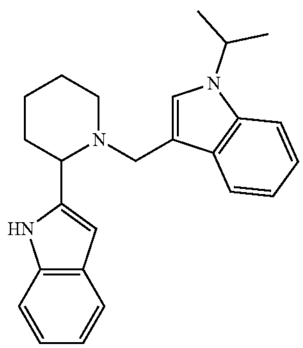 [SMILES: CC(C)n1cc(CN2CCCCC2c2cc3ccccc3[nH]2)c2ccccc21] | 371.53 | 373 | 3.94[3] | +++ | 3-[2-(1H-Indol-2-yl)-piperidin-1-ylmethyl]-1-isopropyl-1H-indole | |
| 10 | 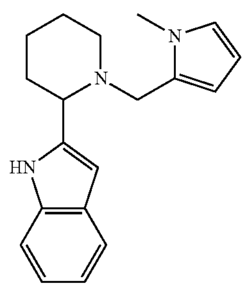 [SMILES: Cn1cccc1CN1CCCCC1c1cc2ccccc2[nH]1] | 293.41 | 294 | 2.85[3] | ++ | 2-[1-(1-Methy-1H-pyrrol-2-ylmethyl)-piperidin-2-yl]-1H-indole | |
| 13 | 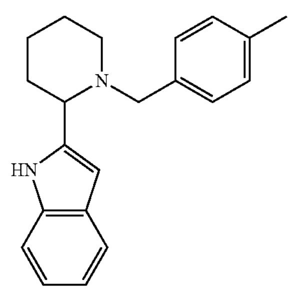 [SMILES: Cc1ccc(CN2CCCCC2c2cc3ccccc3[nH]2)cc1] | 304.43 | 305 | 3.74[3] | ++++ | 2-[1-(4-Methyl-benzyl)-piperidin-2-yl]-1H-indole | |
| 14 | 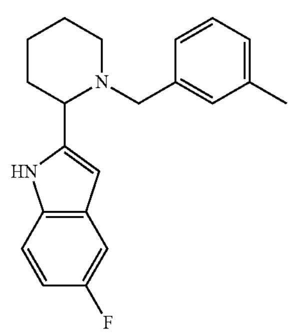 [SMILES: Cc1cccc(CN2CCCCC2c2cc3cc(F)ccc3[nH]2)c1] | 322.42 | 323 | 3.82[3] | +++ | 5-Fluoro-2-[1-(3-methyl-benzyl)-piperidin 2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 15 | 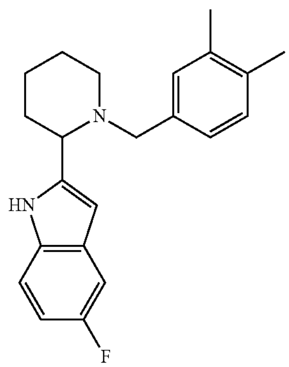 [SMILES: Cc1ccc(CN2CCCCC2c2cc3cc(F)ccc3[nH]2)cc1C] | 336.45 | 337 | 4.07[3] | +++ | 2-[1-(3,4-Dimethyl-benzyl)-piperidin-2-yl]-5-fluoro-1H-indole | |
| 16 | 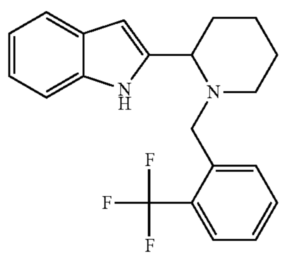 [SMILES: FC(F)(F)c1ccccc1CN1CCCCC1c1cc2ccccc2[nH]1] | 358.40 | 359 | 3.91[3] | ++ | 2-[1-(2-Trifluoro-methyl-benzyl)-piperidin-2-yl]-1H-indole | |
| 17 | 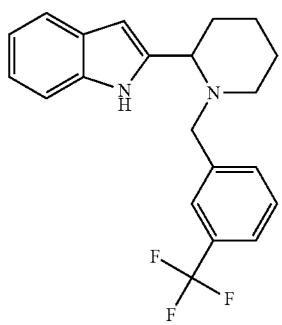 [SMILES: FC(F)(F)c1cccc(CN2CCCCC2c2cc3ccccc3[nH]2)c1] | 358.40 | 359 | 4.05[3] | ++ | 2-[1-(3-Trifluoro-methyl-benzyl)-piperidin-2-yl]-1H-indole | |
| 18 | 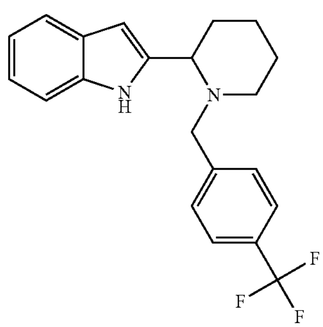 [SMILES: FC(F)(F)c1ccc(CN2CCCCC2c2cc3ccccc3[nH]2)cc1] | 358.40 | 359 | 4.08[3] | +++ | 2-[1-(4-Trifluoro-methyl-benzyl)-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 19 | 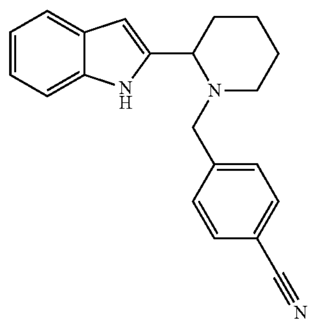 [SMILES: N#Cc1ccc(CN2CCCCC2c2cc3ccccc3[nH]2)cc1] | 315.42 | 316 | 3.34[3] | ++ | 4-[2-(1H-Indol-2-yl)-piperidin-1-ylmethyl]-benzonitrile | |
| 20 | 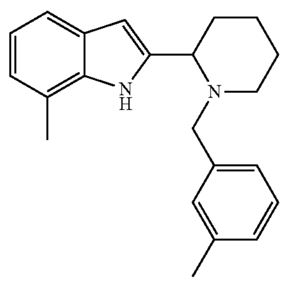 [SMILES: Cc1cccc(CN2CCCCC2c2cc3cccc(C)c3[nH]2)c1] | 318.46 | 319 | 4.00[3] | +++ | 7-Methyl-2-[1-(3-methyl-benzyl)-piperidin-2-yl]-1H-indole | |
| 21 | 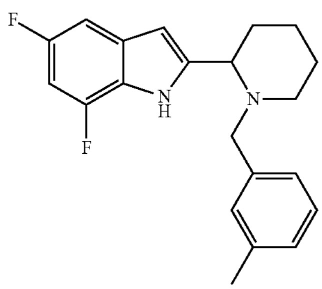 [SMILES: Cc1cccc(CN2CCCCC2c2cc3cc(F)cc(F)c3[nH]2)c1] | 340.41 | 341 | 3.93[3] | ++ | 5,7-Difluoro-2-[1-(3-methyl-benzyl)-piperidin-2-yl]-1H-indole | |
| 22 | 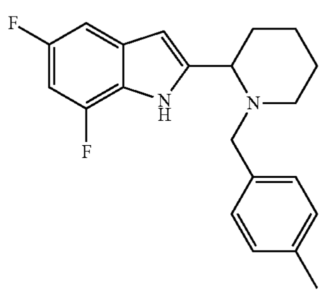 [SMILES: Cc1ccc(CN2CCCCC2c2cc3cc(F)cc(F)c3[nH]2)cc1] | 340.41 | 341 | 3.91[3] | ++ | 5,7-Difluoro-2-[1-(4-methyl-benzyl)-piperidin-2-yl]-1H-indole | |
| 23 | 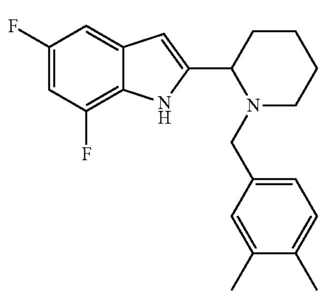 [SMILES: Cc1ccc(CN2CCCCC2c2cc3cc(F)cc(F)c3[nH]2)cc1C] | 354.44 | 355 | 4.18[3] | +++ | 2-[1-(3,4-Dimethyl-benzyl)-piperidin-2-yl]-5,7-difluoro-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 24 | 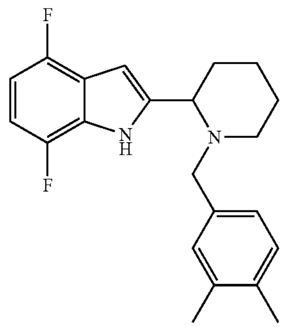 [SMILES: Cc1ccc(CN2CCCCC2c2cc3c(F)ccc(F)c3[nH]2)cc1C] | 354.44 | 355 | 4.11[3] | +++ | 2-[1-(3,4-Dimethyl-benzyl)-piperidin-2-yl]-4,7-difluoro-1H-indole | |
| 25 | 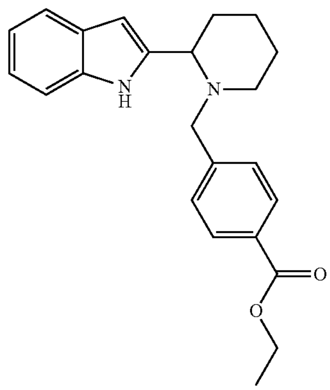 [SMILES: CCOC(=O)c1ccc(CN2CCCCC2c2cc3ccccc3[nH]2)cc1] | 362.47 | 363 | 3.743[3] | +++ | 4-[2-(1H-Indol-2-yl)-piperidin-1-ylmethyl]-benzoic acid ethyl ester | |
| 26 | 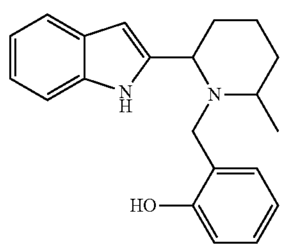 [SMILES: CC1CCCC(c2cc3ccccc3[nH]2)N1Cc1ccccc1O] | 320.43 | 321 | 3.17[3] | +++ | 2-[2-(1H-Indol-2-yl)-6-methyl-piperidin-1-ylmethyl]-phenol | |
| 27 | 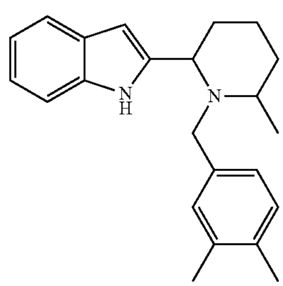 [SMILES: Cc1ccc(CN2C(C)CCCC2c2cc3ccccc3[nH]2)cc1C] | 332.49 | 333 | 3.67[3] | ++++ | 2-[1-(3,4-Dimethyl-benzyl)-6-methyl-piperidin-2-yl]-1H-indole | |
| 28 | 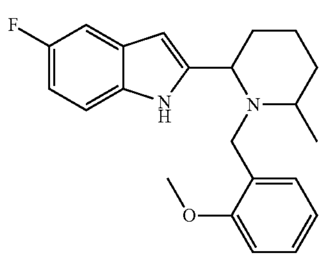 [SMILES: COc1ccccc1CN1C(C)CCCC1c1cc2cc(F)ccc2[nH]1] | 352.45 | 353 | 3.94[3] | +++ | 5-Fluoro-2-[1-(2-methoxy-benzyl)-6-methyl-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 29 | 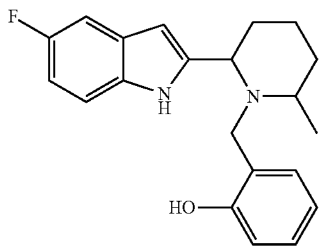 [SMILES: CC1CCCC(c2cc3cc(F)ccc3[nH]2)N1Cc1ccccc1O] | 338.42 | 339 | 3.16[3] | +++ | 2-[2-(5-Fluoro-1H-indol-2-yl)-6-methyl-piperidin-1-ylmethyl]-phenol | |
| 30 | 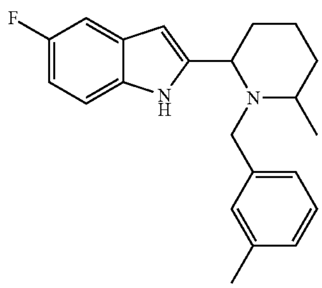 [SMILES: Cc1cccc(CN2C(C)CCCC2c2cc3cc(F)ccc3[nH]2)c1] | 336.45 | 337 | 3.52[3] | ++++ | 5-Fluoro-2-[6-methyl-1-(3-methyl-benzyl)-piperidin-2-yl]-1H-indole | |
| 31 | 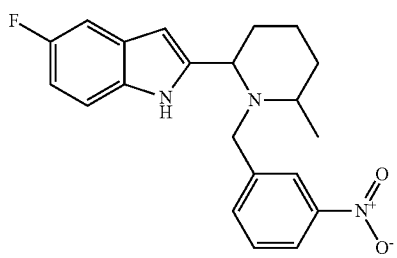 [SMILES: CC1CCCC(c2cc3cc(F)ccc3[nH]2)N1Cc1cccc([N+](=O)[O-])c1] | 367.42 | 368 | 3.09[3] | +++ | 5-Fluoro-2-[6-methyl-1-(3-nitro-benzyl)-piperidin-2-yl]-1H-indole | |
| 32 | 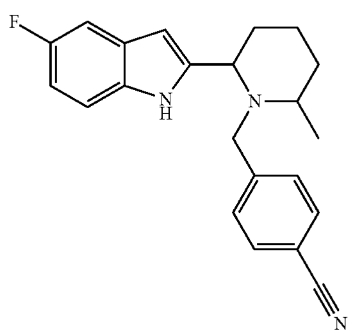 [SMILES: CC1CCCC(c2cc3cc(F)ccc3[nH]2)N1Cc1ccc(C#N)cc1] | 347.43 | 348 | 2.98[3] | +++ | 4-[2-(5-Fluoro-1H-indol-2-yl)-6-methyl-piperidin-1-ylmethyl]-benzonitrile | |
| 33 | 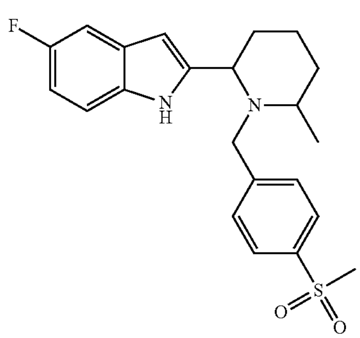 [SMILES: CC1CCCC(c2cc3cc(F)ccc3[nH]2)N1Cc1ccc(S(C)(=O)=O)cc1] | 400.52 | 402 | 2.71[3] | +++ | 5-Fluoro-2-[1-(4-methanesulfonyl-benzyl)-6-methyl-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 34 | 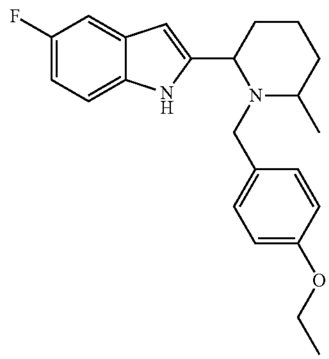 [SMILES: CCOc1ccc(CN2C(C)CCCC2c2cc3cc(F)ccc3[nH]2)cc1] | 366.48 | 367 | 3.67[3] | +++ | 2-[1-(4-Ethoxy-benzyl)-6-methyl-piperidin-2-yl]-5-fluoro-1H-indole | |
| 35 | 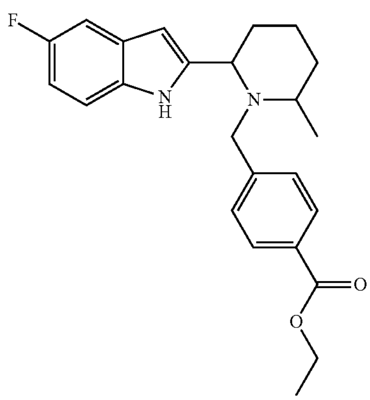 [SMILES: CCOC(=O)c1ccc(CN2C(C)CCCC2c2cc3cc(F)ccc3[nH]2)cc1] | 394.49 | 395 | 3.40[3] | +++ | 4-[2-(5-Fluoro-1H-indol-2-yl)-6-methyl-piperidin-1-ylmethyl]-benzoic acid ethyl ester | |
| 36 | 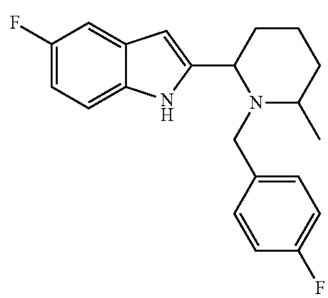 [SMILES: CC1CCCC(c2cc3cc(F)ccc3[nH]2)N1Cc1ccc(F)cc1] | 340.41 | 341 | 3.73[3] | ++++ | 5-Fluoro-2-[1-(4-fluoro-benzyl)-6-methyl-piperidin-2-yl]-1H-indole | |
| 37 | 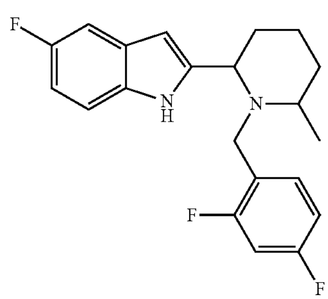 [SMILES: CC1CCCC(c2cc3cc(F)ccc3[nH]2)N1Cc1ccc(F)cc1F] | 358.40 | 359 | 3.33[3] | +++ | 2-[1-(2,4-Difluoro-benzyl)-6-methyl-piperidin-2-yl]-5-fluoro-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 38 | 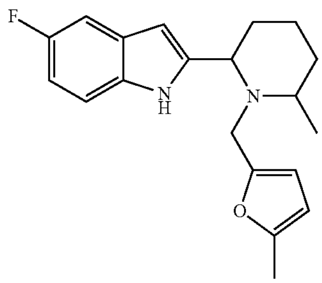 [SMILES: Cc1ccc(CN2C(C)CCCC2c2cc3cc(F)ccc3[nH]2)o1] | 326.41 | 327 | 3.38[3] | ++++ | 5-Fluoro-2-[6-methyl-1-(5-methyl-furan-2-ylmethyl)-piperidin-2-yl]-1H-indole | |
| 39 | 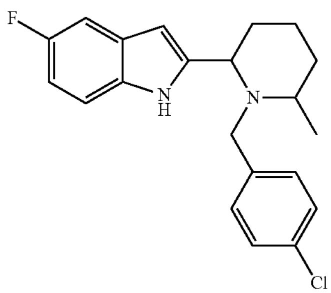 [SMILES: CC1CCCC(c2cc3cc(F)ccc3[nH]2)N1Cc1ccc(Cl)cc1] | 356.87 | 358 | 3.99[3] | +++ | 2-[1-(4-Chloro-benzyl)-6-methyl-piperidin-2-yl]-5-fluoro-1H-indole | |
| 40 | 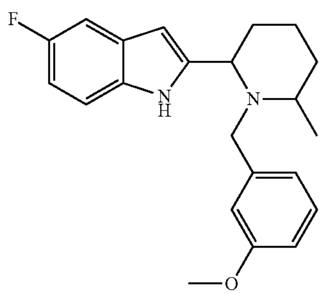 [SMILES: COc1cccc(CN2C(C)CCCC2c2cc3cc(F)ccc3[nH]2)c1] | 352.42 | 353 | 3.32[3] | ++++ | 5-Fluoro-2-[1-(3-methoxy-benzyl)-6-methyl-piperidin-2-yl]-1H-indole | |
| 41 | 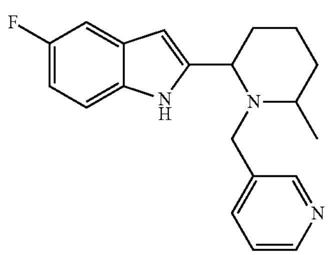 [SMILES: CC1CCCC(c2cc3cc(F)ccc3[nH]2)N1Cc1cccnc1] | 323.41 | 324 | 2.34[3] | +++ | 5-Fluoro-2-(6-methyl-1-pyridin-3-ylmethyl-piperidin-2-yl)-1H-indole | |
| 42 | 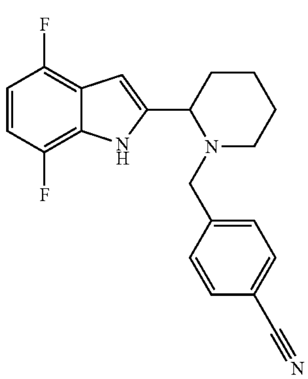 [SMILES: N#Cc1ccc(CN2CCCCC2c2cc3c(F)ccc(F)c3[nH]2)cc1] | 351.41 | 352 | 3.49[3] | ++ | 4-[2-(4,7-Difluoro-1H-indol-2-yl)-piperidin-1-ylmethyl]-benzonitrile | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 44 | 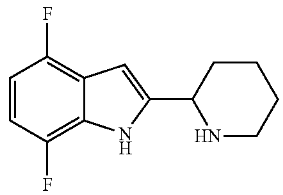 [SMILES: Fc1ccc(F)c2[nH]c(C3CCCCN3)cc12] | 236.26 | 237 | 2.25[3] | +++ | 4,7-Difluoro-2-piperidin-2-yl-1H-indole | |
| 45 | 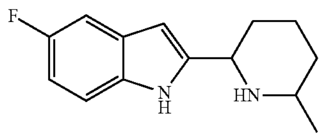 [SMILES: CC1CCCC(c2cc3cc(F)ccc3[nH]2)N1] | 232.30 | 233 | 2.29[3] | +++ | 5-Fluoro-2-(6-methyl-piperidin-2-yl)-1H-indole | 1H NMR (400 MHz; CDCl[3]) δ 10.70 (s, 1H), 7.90 (s, 1H), 7.30-7.20 (m, 1H), 7.16 (dd, J = 7.7, 1.2, 1H), 6.92-6.83 (m, 1H), 6.35 (s, 1H), 4.08 (dd, J = 6.5, 1.5, 1H), 2.90-2.78 (m, 1H), 2.10-1.90 (m, 3H), 1.99-1.89 (m, 1H), 1.70-1.60 (m, 1H), 1.36.1.23 (m, 1H), 0.73 (d, J = 4.5, 3H). |
| 46 | 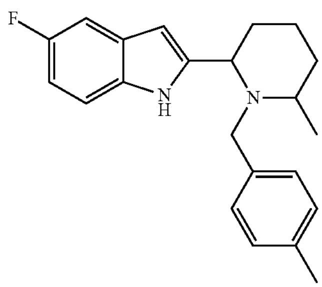 [SMILES: Cc1ccc(CN2C(C)CCCC2c2cc3cc(F)ccc3[nH]2)cc1] | 336.45 | 337 | 3.57[3] | +++ | 5-Fluoro-2-[6-methyl-1-(4-methyl-benzyl)-piperidin-2-yl]-1H-indole | |
| 47 | 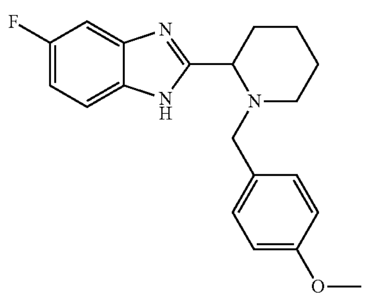 [SMILES: COc1ccc(CN2CCCCC2c2nc3cc(F)ccc3[nH]2)cc1] | 339.41 | 340 | 2.67[1] 1.57[2] | +++ | 5-Fluoro-2-[1-(4-methoxy-benzyl)-piperidin-2-yl]-1H-benzoimidazole | |
| 48 | 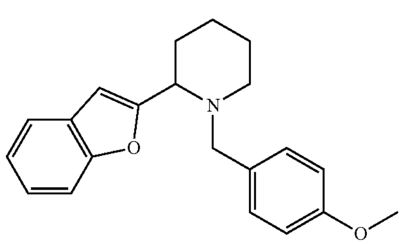 [SMILES: COc1ccc(CN2CCCCC2c2cc3ccccc3o2)cc1] | 321.42 | 322 | 2.85[1] 1.67[2] | +++ | 2-Benzofuran-2-yl-1-(4-methoxy-benzyl)-piperidine | 1H NMR (400 MHz, DMSO) δ 7.57 (dd, J = 10.2, 8.5, 2H), 7.28-7.18 (m,2H), 7.14 (d, J = 8.5, 2H), 6.85-6.80 (m, 3H), 3.70 (s, 3H), 3.58 (d, J =13.0, 1H), 3.53 (t, J = 6.0, 1H), 3.05 (d, J = 13.3, 1H), 2.84-2.78 (m, 1H), 2.08-1.98 (m, 1H), 1.89-1.72 (m, 3H), 1.62-1.31 (m, 3H). |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 49 | 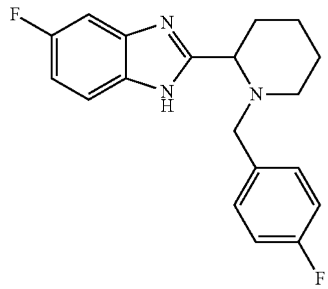 | 327.38 | 328 | 2.69[1]<br>1.57[2] | ++++ | 5-Fluoro-2-[1-(4-fluoro-benzyl)-piperidin-2-yl]-1H-benzo-imidazole | $^1$H NMR (400 MHz, DMSO, TFA exchanged) δ 7.69 (dd, J = 8.9, 4.7 Hz, 1H), 7.49 (dd, J = 9.1, 2.4 Hz, 1H), 7.46-7.41 (m, 2H), 7.19-7.11 (m, 3H), 4.69 (d, J = 8.4 Hz, 1H), 4.33 (d, J = 13.1 Hz, 1H), 4.18 (d, J = 13.2 Hz, 1H), 3.47-3.36 (m, 1H), 3.20-3.08 (m, 1H), 2.28-2.19 (m, 1H), 2.19-2.04 (m, 1H), 1.89-1.77 (m, 3H), 1.65-1.53 (m, 1H). |
| 50 | 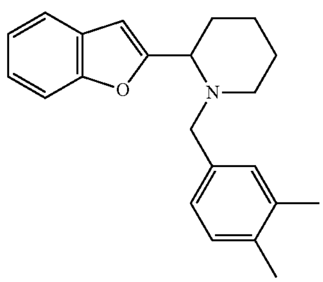 [SMILES: Cc1ccc(CN2CCCCC2c2cc3ccccc3o2)cc1C] | 319.45 | 320 | 3.12[1]<br>1.76[2] | +++ | 2-Benzofuran-2-yl-1-(3,4-dimethyl-benzyl)-piperidine | |
| 51 | 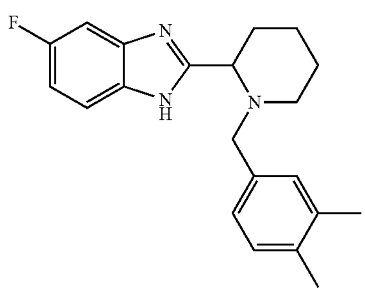 [SMILES: Cc1ccc(CN2CCCCC2c2nc3cc(F)ccc3[nH]2)cc1C] | 337.44 | 338 | 2.99[1]<br>1.66[2] | ++++ | 2-[1-(3,4-Dimethyl-benzyl)-piperidin-2-yl]-5-fluoro-1H-benzo-imidazole | $^1$H NMR (400 MHz, DMSO, TFA exchanged) δ 7.74 (dd, J = 8.9, 4.8 Hz, 1H), 7.50 (dd, J = 9.1, 2.4 Hz, 1H), 7.26-7.15 (m, 1H), 7.18-7.06 (m, 3H), 4.77 (d, J = 8.2 Hz, 1H), 4.46-4.19 (m, 2H), 3.57 (d, J = 12.1 Hz, 1H), 3.30-3.17 (m, 1H), 2.37-2.25 (m, 1H), 2.25-1.99 (m, 1H), 2.19 (s, 6H), 1.96-1.85 (m, 3H), 1.77-1.60 (m, 1H). |
| 52 | 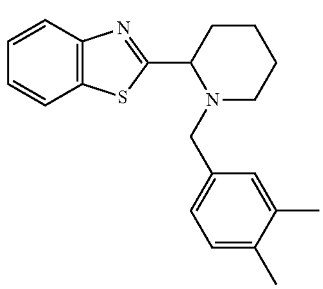 [SMILES: Cc1ccc(CN2CCCCC2c2nc3ccccc3s2)cc1C] | 336.50 | 338 | 3.55[1]<br>2.01[2] | ++ | 2-[1-(3,4-Dimethyl-benzyl)-piperidin-2-yl]-benzo-thiazole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 54 | 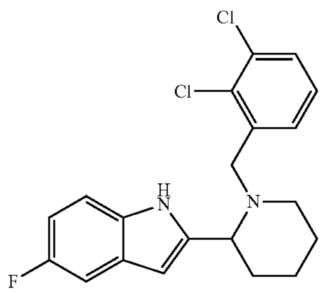 [SMILES: Fc1ccc2[nH]c(C3CCCCN3Cc3cccc(Cl)c3Cl)cc2c1] | 377.29 | 378 | 3.80[3] | +++ | 2-[1-(2,3-Dichloro-benzyl)-piperidin-2-yl]-5-fluoro-1H-indole | |
| 55 | 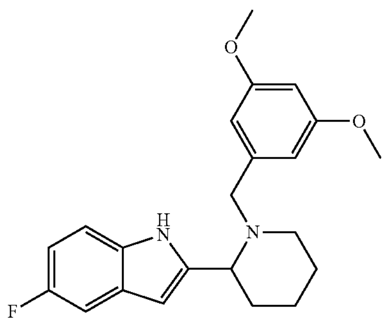 [SMILES: COc1cc(CN2CCCCC2c2cc3cc(F)ccc3[nH]2)cc(OC)c1] | 368.45 | 369 | 3.59[3] | +++ | 2-[1-(3,5-Dimethoxy-benzyl)-piperidin-2-yl]-5-fluoro-1H-indole | |
| 56 | 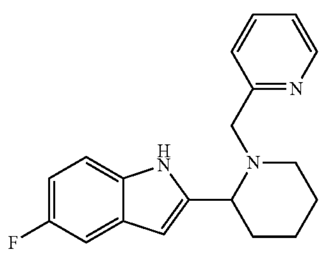 [SMILES: Fc1ccc2[nH]c(C3CCCCN3Cc3ccccn3)cc2c1] | 309.39 | 310 | 2.88[3] | +++ | 5-Fluoro-2-(1-pyridin-2-ylmethyl-piperidin-2-yl)-1H-indole | |
| 57 | 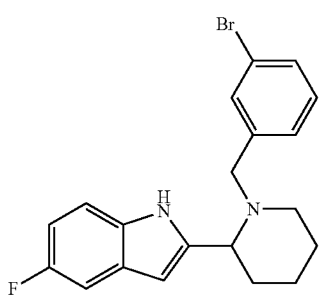 [SMILES: Fc1ccc2[nH]c(C3CCCCN3Cc3cccc(Br)c3)cc2c1] | 387.29 | 388 | 3.73[3] | +++ | 2-[1-(3-Bromo-benzyl)-piperidin-2-yl]-5-fluoro-1H-indole | |
| 58 | 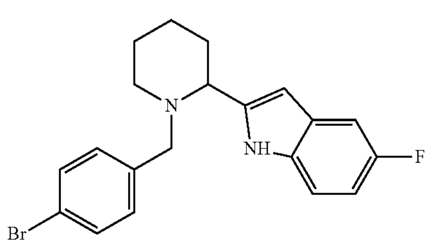 [SMILES: Fc1ccc2[nH]c(C3CCCCN3Cc3ccc(Br)cc3)cc2c1] | 387.29 | 388 | 3.79[3] | +++ | 2-[1-(4-Bromo-benzyl)-piperidin-2-yl]-5-fluoro-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 59 | 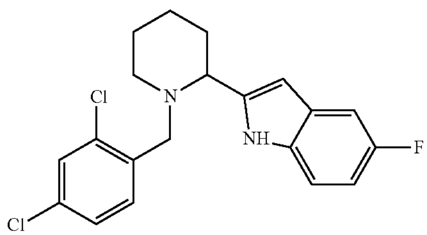 [SMILES: Fc1ccc2[nH]c(C3CCCCN3Cc3ccc(Cl)cc3Cl)cc2c1] | 377.29 | 378 | 3.86[3] | ++ | 2-[1-(2,4-Dichloro-benzyl)-piperidin-2-yl]-5-fluoro-1H-indole | |
| 60 | 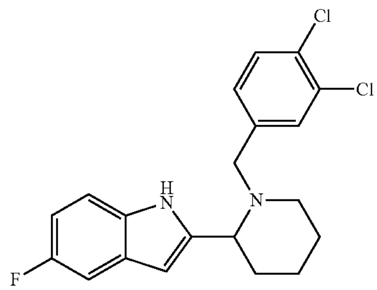 [SMILES: Fc1ccc2[nH]c(C3CCCCN3Cc3ccc(Cl)c(Cl)c3)cc2c1] | 377.29 | 378 | 3.96[3] | ++ | 2-[1-(3,4-Dichloro benzyl)-piperidin-2-yl]-5-fluoro-1H-indole | |
| 61 | 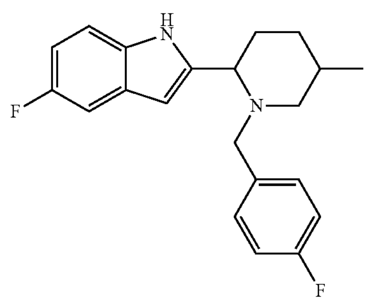 [SMILES: CC1CCC(c2cc3cc(F)ccc3[nH]2)N(Cc2ccc(F)cc2)C1] | 340.41 | 341 | 3.63[3] | +++ | 5-Fluoro-2-[1-(4-fluoro-benzyl)-5-methyl-piperidin-2-yl]-1H-indole | |
| 62 | 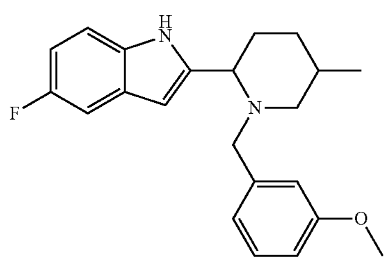 [SMILES: COc1cccc(CN2CC(C)CCC2c2cc3cc(F)ccc3[nH]2)c1] | 352.45 | 353 | 3.65[3] | ++ | 5-Fluoro-2-[1-(3-methoxy-benzyl)-5-methyl-piperidin-2-yl]-1H-indole | |
| 63 | 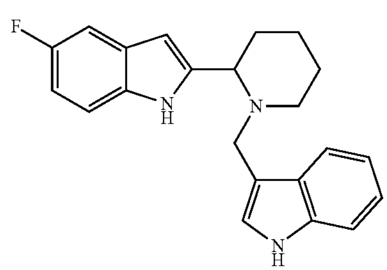 [SMILES: Fc1ccc2[nH]c(C3CCCCN3Cc3c[nH]c4ccccc34)cc2c1] | 347.43 | 348 | 3.46[3] | +++ | 5-Fluoro-2-[1-(1H-indol-3-ylmethyl)-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 64 | 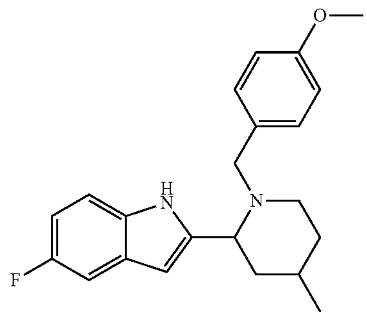 [SMILES: COc1ccc(CN2CCC(C)CC2c2cc3cc(F)ccc3[nH]2)cc1] | 352.45 | 353 | 3.66[3] | +++ | 5-Fluoro-2-[1-(4-methoxy-benzyl)-4-methyl-piperidin-2-yl]-1H-indole | |
| 65 | 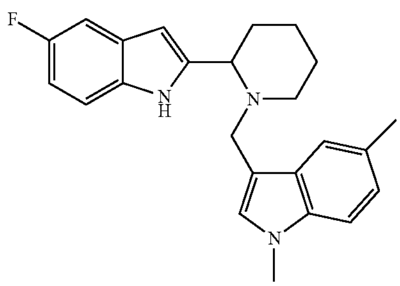 [SMILES: Cc1ccc2c(c1)c(CN1CCCCC1c1cc3cc(F)ccc3[nH]1)cn2C] | 375.49 | 376 | 3.94[3] | +++ | 3-[2-(5-Fluoro-1H-indol-2-yl)-piperidin-1-ylmethyl]-1,5-dimethyl-1H-indole | |
| 66 | 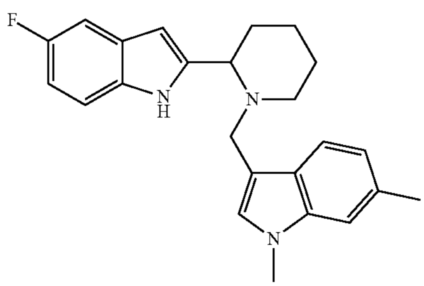 [SMILES: Cc1ccc2c(CN3CCCCC3c3cc4cc(F)ccc4[nH]3)cn(C)c2c1] | 375.49 | 376 | 3.90[3] | +++ | 3-[2-(5-Fluoro-1H-indol-2-yl)-piperidin-1-ylmethyl]-1,6-dimethyl-1H-indole | |
| 67 | 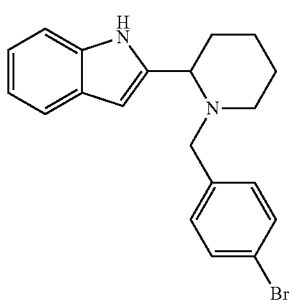 [SMILES: Brc1ccc(CN2CCCCC2c2cc3ccccc3[nH]2)cc1] | 369.30 | 370 | 3.63[3] | +++ | 2-[1-(4-Bromo-benzyl)-piperidin-2-yl]-1H-indole | |
| 68 | 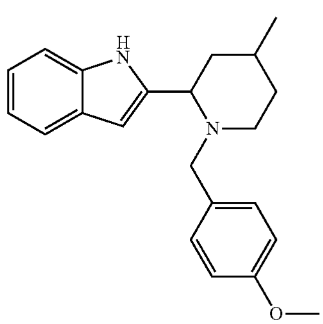 [SMILES: COc1ccc(CN2CCC(C)CC2c2cc3ccccc3[nH]2)cc1] | 334.46 | 335 | 3.56[3] | +++ | 2-[1-(4-Methoxy-benzyl)-4-methyl-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 69 | 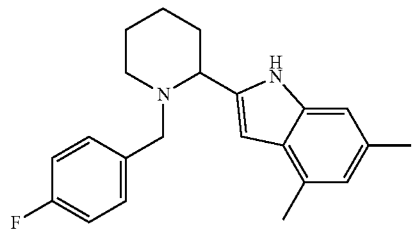 [SMILES: Cc1cc(C)c2cc(C3CCCCN3Cc3ccc(F)cc3)[nH]c2c1] | 336.45 | 337 | 3.89[3] | +++ | 2-[1-(4-Fluoro-benzyl)-piperidin-2-yl]-4,6-dimethyl-1H-indole | |
| 70 | 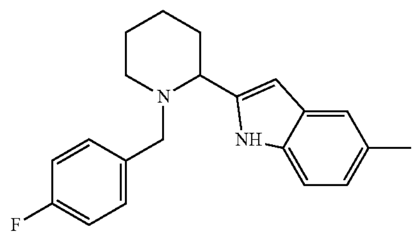 [SMILES: Cc1ccc2[nH]c(C3CCCCN3Cc3ccc(F)cc3)cc2c1] | 322.42 | 323 | 3.57[3] | +++ | 2-[1-(4-Fluoro-benzyi)-piperidin-2-yl]-5-methyl-1H-indole | |
| 71 | 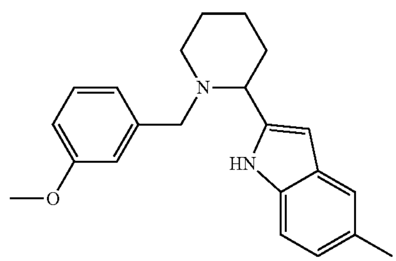 | 334.46 | 335 | 3.63[3] | +++ | 2-[1-(3-Methoxy-benzyl)-piperidin-2-yl]-5-methyl-1H-indole | |
| 72 | 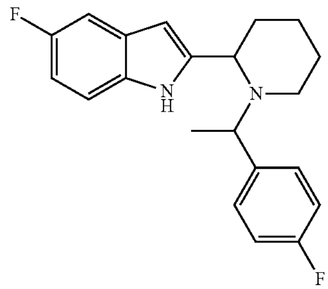 [SMILES: CC(c1ccc(F)cc1)N1CCCCC1c1cc2cc(F)ccc2[nH]1] | 340.41 | 341 | 3.86[3] | ++++ | 5-Fluoro-2-{1-[1-(4-fluoro-phenyl)-ethyl]-piperidin-2-yl}-1H-indole | |
| 73 | 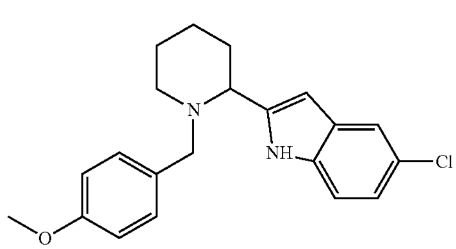 [SMILES: COc1ccc(CN2CCCCC2c2cc3cc(Cl)ccc3[nH]2)cc1] | 354.88 | 356 | 3.91[3] | ++++ | 5-Chloro-2-[1-(4-methoxy-benzyl)-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 74 | 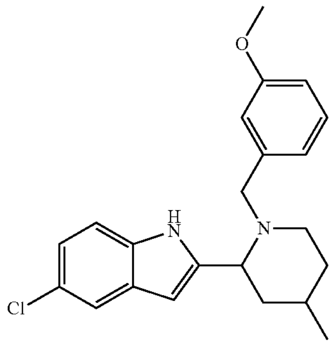 [SMILES: COc1cccc(CN2CCC(C)CC2c2cc3cc(Cl)ccc3[nH]2)c1] | 368.91 | 370 | 4.00[3] | +++ | 5-Chloro-2-[1-(3-methoxy-benzyl)-4-methyl-piperidin-2-yl]-1H-indole | |
| 75 | 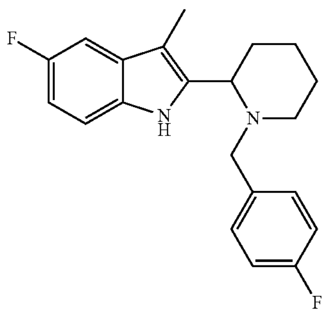 [SMILES: Cc1c(C2CCCCN2Cc2ccc(F)cc2)[nH]c2ccc(F)cc12] | 340.41 | 341 | 3.86[3] | ++++ | 5-Fluoro-2-[1-(4-fluoro-benzyl)-piperidin-2-yl]-3-methyl-1H-indole | |
| 76 | 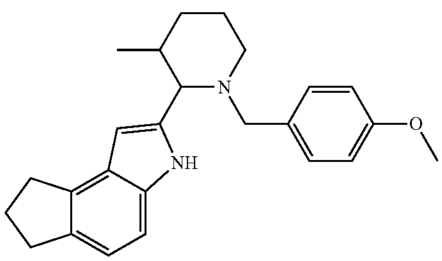 [SMILES: COc1ccc(CN2CCCC(C)C2c2cc3c4c(ccc3[nH]2)CCC4)cc1] | 374.53 | 376 | 3.81[3] | ++ | 2-[1-(4-Methoxy-benzyl)-3-methyl-piperidin-2-yl]-3,6,7,8-tetrahydro-cyclopenta[e]indole | |
| 79 | 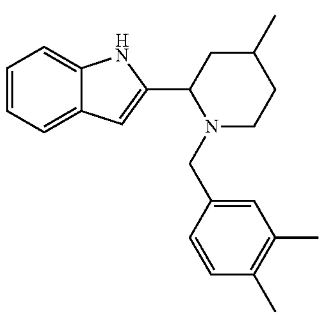 [SMILES: Cc1ccc(CN2CCC(C)CC2c2cc3ccccc3[nH]2)cc1C] | 332.49 | 333 | 4.05[3] | +++ | 2-[1-(3,4-Dimethyl-benzyl)-4-methyl-piperidin-2-yl]-1H-indole | |
| 81 | 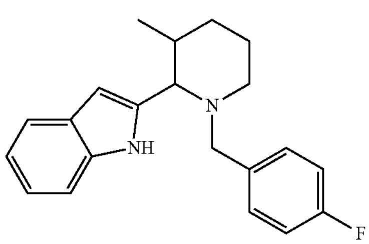 [SMILES: CC1CCCN(Cc2ccc(F)cc2)C1c1cc2ccccc2[nH]1] | 322.42 | 323 | 3.66[3] | +++ | 2-[1-(4-Fluoro-benzyl)-3-methyl-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 82 | 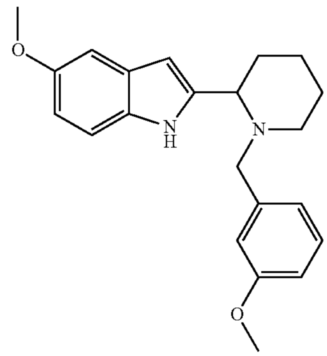 [SMILES: COc1cccc(CN2CCCCC2c2cc3cc(OC)ccc3[nH]2)c1] | 350.46 | 351 | 3.06[3] | ++++ | 5-Methoxy-2-[1-(3-methoxy-benzyl)-piperidin-2-yl]-1H-indole | |
| 83 | 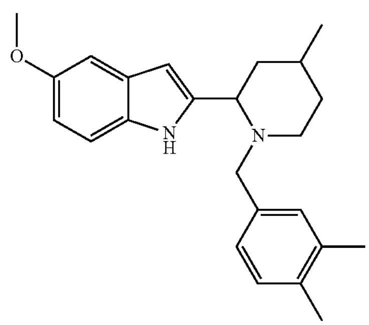 [SMILES: COc1ccc2[nH]c(C3CC(C)CCN3Cc3ccc(C)c(C)c3)cc2c1] | 362.51 | 364 | 3.74[3] | +++ | 2-[1-(3,4-Dimethyl-benzyl)-4-methyl-piperidin-2-yl]-5-methoxy-1H-indole | |
| 84 | 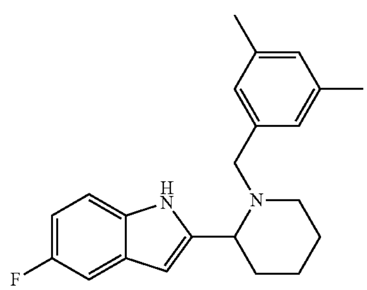 [SMILES: Cc1cc(C)cc(CN2CCCCC2c2cc3cc(F)ccc3[nH]2)c1] | 336.45 | 337 | 4.00[3] | ++++ | 2-[1-(3,5-Dimethyl-benzyl)-piperidin-2-yl]-5-fluoro-1H-indole | |
| 85 | 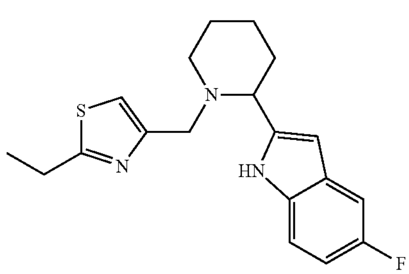 [SMILES: CCc1nc(CN2CCCCC2c2cc3cc(F)ccc3[nH]2)cs1] | 343.47 | 344 | 3.47[3] | ++++ | 2-[1-(2-Ethyl-thiazol-4-ylmethyl)-piperidin-2-yl]-5-fluoro-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 86 | 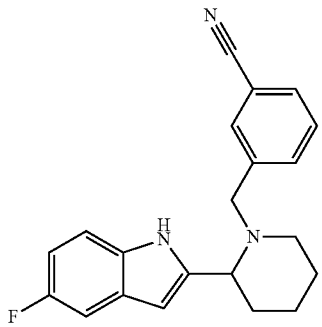 [SMILES: N#Cc1cccc(CN2CCCCC2c2cc3cc(F)ccc3[nH]2)c1] | 333.41 | 334 | 3.05[3] | +++ | 3-[2-(5-Fluoro-1H-indol-2-yl)-piperidin-1-ylmethyl]-benzonitrile | |
| 87 | 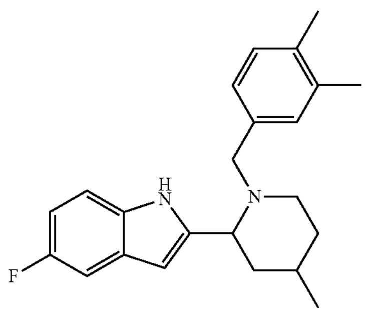 [SMILES: Cc1ccc(CN2CCC(C)CC2c2cc3cc(F)ccc3[nH]2)cc1C] | 350.48 | 351 | 3.95[3] | ++++ | 2-[1-(3,4-Dimethyl-benzyl)-4-methyl-piperidin-2-yl]-5-fluoro-1H-indole | |
| 88 | 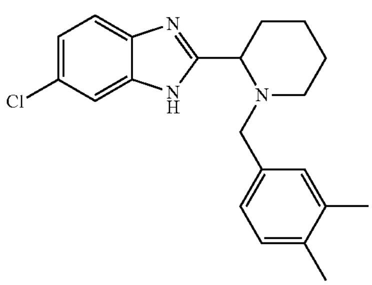 [SMILES: Cc1ccc(CN2CCCCC2c2nc3ccc(Cl)cc3[nH]2)cc1C] | 353.89 | 355 | 3.20[1] | ++++ | 6-Chloro-2-[1-(3,4-dimethyl-benzyl)-piperidin-2-yl]-1H-benzo-imidazole | $^1$H NMR (400 MHz, DMSO) δ 13.18 (s, 1H), 7.83-7.67 (m, 2H), 7.37-7.30 (m, 1H), 7.26-7.08 (m, 3H), 4.62 (d, J = 9.1, 1H), 4.21 (d, J = 13.2, 2H), 3.42-3-02 (m, 2H), 2.28-2.06 (m, 7H), 1.92-1.78 (m, 2H), 1.71-1.54 (m, 1H), 1.32-1.13 (m, 2H). |
| 89 | 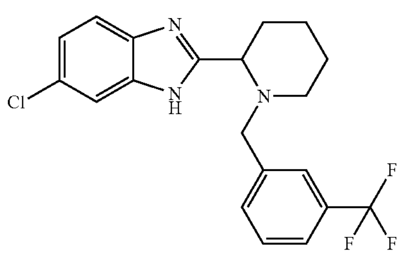 [SMILES: FC(F)(F)c1cccc(CN2CCCCC2c2nc3ccc(Cl)cc3[nH]2)c1] | 393.84 | 395 | 3.49[1] | +++ | 6-Chloro-2-[1-(3-trifluoro-methyl-benzyl)-piperidin-2-yl]-1H-benzo-imidazole | |
| 90 | 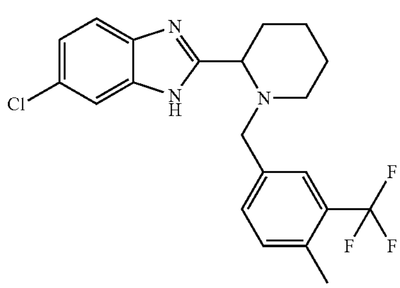 [SMILES: Cc1ccc(CN2CCCCC2c2nc3ccc(Cl)cc3[nH]2)cc1C(F)(F)F] | 407.86 | 409 | 3.47[1] | +++ | 6-Chloro-2-[1-(4-methyl-3-trifluoro-methyl-benzyl)-piperidin-2-yl]-1H-benzo-imidazole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 91 | 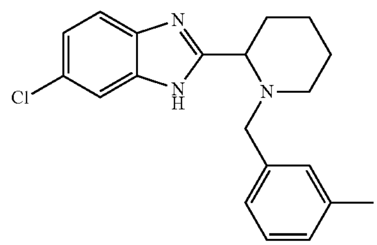 [SMILES: Cc1cccc(CN2CCCCC2c2nc3ccc(Cl)cc3[nH]2)c1] | 339.87 | 341 | 2.85[1] | ++++ | 6-Chloro 2-[1-(3-methyl-benzyl)-piperidin-2-yl]-1H-benzo-imidazole | $^1$H NMR (500 MHz, DMSO, TFA exchanged) δ 7.74 (d, J = 1.6 Hz, 1H), 7.65 (d, J = 8.7 Hz, 1H), 7.31 (dd, J = 8.7, 1.9 Hz, 1H), 7.21-7.09 (m, 4H), 4.73 (d, J = 8.8 Hz, 1H), 4.29 (d, J = 13.0 Hz, 1H), 4.15 (d, J = 13.0 Hz, 1H), 3.45 (s, 1H), 3.16 (t, J = 11.1 Hz, 1H), 2.27-2.07 (m, 6H), 1.84 (d, J = 29.1 Hz, 3H), 1.64-1.53 (m, 1H). |
| 92 | 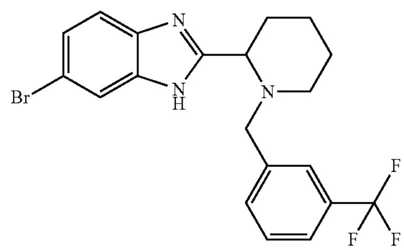 | 438.29 | 439 | 3.60[1] 1.88[2] | +++ | 6-Bromo-2-[1-3-trifluoromethyl-benzyl)-piperidin-2-yl]-1H-benzo-imidazole | $^1$H NMR (500 MHz, DMSO) δ 7.88 (d, J = 1.7, 1H), 7.81 (s, 1H), 7.77 (d, J = 7.7, 1H), 7.73 (d, J = 7.9, 1H), 7.65-7.59 (m, 2H), 7.45 (dd, J = 8.6, 1.8, 1H), 4.71 (s, 1H), 4.39 (d, J = 13.0, 1H), 4.30 (s, 1H), 3.85-3.75 (m, 1H), 3.18 (s, 2H), 2.26 (s, 1H), 2.18-2-08 (m, 1H), 1.92-1.78 (m, 3H), 1.63 (s, 1H). |
| 93 | 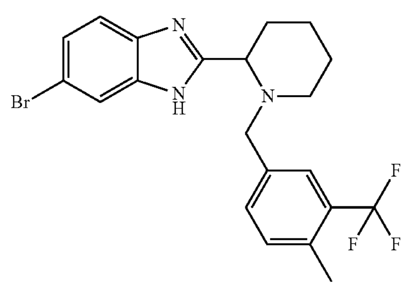 | 452.32 | 453 | 3.63[1] 1.97[2] | +++ | 6-Bromo-2-[1-(4-methyl-3-trifluoro-methyl-benzyl)-piperidin-2-yl]-1H-benzo-imidazole | |
| 94 | 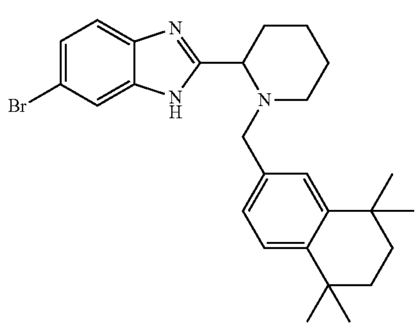 | 480.49 | 481 | 3.89[1] 2.13[2] | ++ | 6-Bromo-2-[1-(5,5,8,8-tetramethyl-5,6,7,8-tetrahydro-naphthalen-2-ylmethyl)-piperidin-2-yl]-1H-benzo-imidazole | |
| 95 | 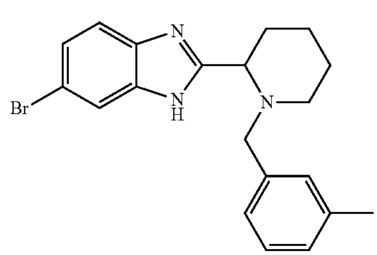 | 384.32 | 385 | 3.07[1] 1.73[2] | ++++ | 6-Bromo-2-[1-(3-methyl-benzyl)-piperidin-2-yl]-1H-benzo-imidazole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 96 | 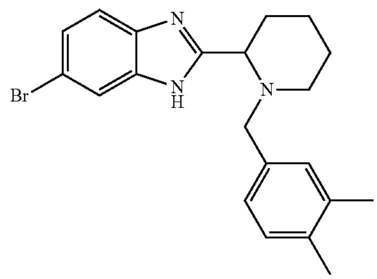 | 398.35 | 399 | 3.15[1]<br>1.75[2] | ++++ | 6-Bromo-2-[1-(3,4-dimethyl-benzyl)-piperidin-2-yl]-1H-benzo-imidazole | |
| 97 | 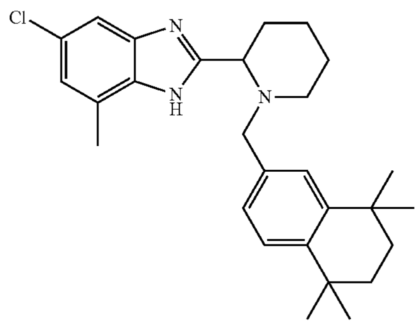 [SMILES: Cc1cc(Cl)cc2nc(C3CCCCN3Cc3ccc4c(c3)C(C)(C)CCC4(C)C)[nH]c12] | 450.07 | 451 | 4.05[1] | +++ | 5-Chloro-7-methyl-2-[1-(5,5,8,8-tetramethyl-5,6,7,8-tetrahydro-naphthalen-2-ylmethyl)-piperidin-2-yl]-1H-benzo-imidazole | |
| 98 | 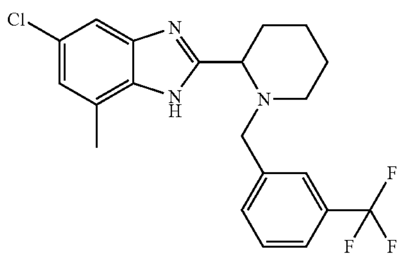 [SMILES: Cc1cc(Cl)cc2nc(C3CCCCN3Cc3cccc(C(F)(F)F)c3)[nH]c12] | 407.86 | 409 | 2.04[2] | +++ | 5-Chloro-7-methyl-2-[1-(3-trifluoromethyl-benzyl)-piperidin-2-yl]-1H-benzo-imidazole | |
| 99 | 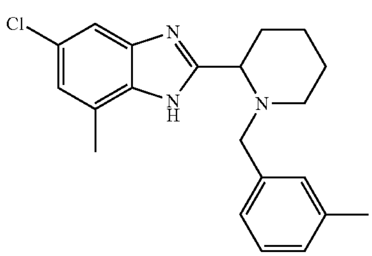 [SMILES: Cc1cccc(CN2CCCCC2c2nc3cc(Cl)cc(C)c3[nH]2)c1] | 353.89 | 355 | 3.15[1]<br>1.77[2] | +++ | 5-Chloro-7-methyl-2-[1-(3-methyl-benzyl)-piperidin-2-yl]-1H-benzo-imidazole | |
| 100 | 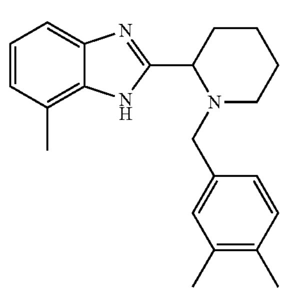 [SMILES: Cc1ccc(CN2CCCCC2c2nc3cccc(C)c3[nH]2)cc1C] | 333.48 | 334 | 3.04[1]<br>1.80[2] | ++++ | 2-[1-(3,4-Dimethyl-benzyl)-piperidin-2-yl]-7-methyl-1H-benzo-imidazole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 101 | 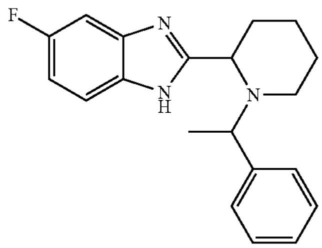 [SMILES: CC(c1ccccc1)N1CCCCC1c1nc2cc(F)ccc2[nH]1] | 323.41 | 324 | 2.43[1]<br>1.48[2] | +++ | 5-Fluoro-2-[1-(1-phenyl-ethyl)-piperidin-2-yl]-1H-benzo-imidazole | |
| 102 | 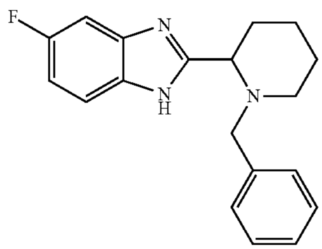 [SMILES: Fc1ccc2[nH]c(C3CCCCN3Cc3ccccc3)nc2c1] | 309.39 | 310 | 2.37[1]<br>1.48[2] | +++ | 2-(1-Benzyl-piperidin-2-yl)-5-fluoro-1H-benzo-imidazole | |
| 103 | 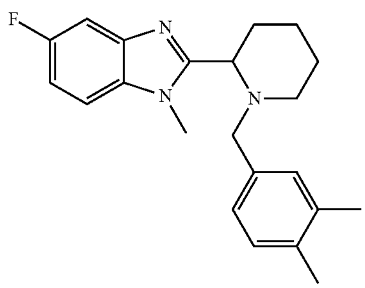 [SMILES: Cc1ccc(CN2CCCCC2c2nc3cc(F)ccc3n2C)cc1C] | 351.47 | 352 | 2.91[1]<br>1.68[2] | +++ | 2-[1-(3,4-Dimethyl-benzyl)-piperidin-2-yl]-5-fluoro-1-methyl-1H-benzo-imidazole | |
| 104 | 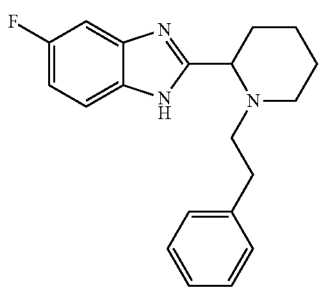 [SMILES: Fc1ccc2[nH]c(C3CCCCN3CCc3ccccc3)nc2c1] | 323.41 | 324 | 2.64[1] | +++ | 5-Fluoro-2-(1-phenethyl-piperidin-2-yl)-1H-benzo-imidazole | |
| 105 | 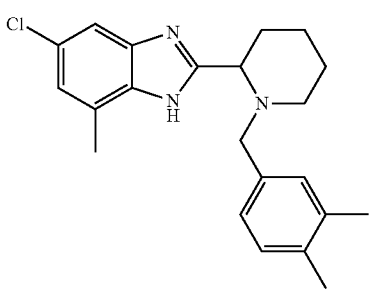 [SMILES: Cc1ccc(CN2CCCCC2c2nc3cc(Cl)cc(C)c3[nH]2)cc1C] | 367.92 | 369 | 3.25[1]<br>1.85[2] | +++ | 5-Chloro-2-[1-(3,4-dimethyl-benzyl)-piperidin-2-yl]-7-methyl-1H-benzo-imidazole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 106 | 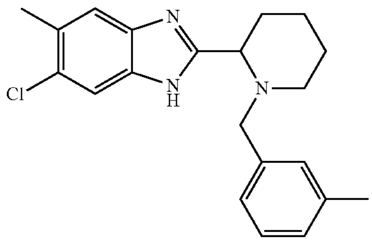 | 353.89 | 355 | 3.09[1]<br>1.81[2] | ++++ | 6-Chloro-5-methyl-2-[1-(3-methyl-benzyl)-piperidin-2-yl]-1H-benzo-imidazole | $^1$H NMR (400 MHz, DMSO) δ 12.46 (s, 1H), 7.64-7.38 (m, 2H), 7.19-7.13 (m, 1H), 7.10-706 (m, 2H), 7.01 (d, J = 7.4, 1H), 3.58-3.52 (m, 1H), 3.42-3.40 (m, 1H), 3.00 (d, J = 13.3, 1H), 2.90-2.83 (m, 1H), 2.39 (s, 3H), 2.26 (s, 3H), 2.00 (td, J = 11.3, 2.6, 1H), 1.87-1.74 (m, 3H), 1.65-1.57 (m, 1H), 1.54-1.42 (m, 1H), 1.42-1.30 (m, 1H). |
| 107 | 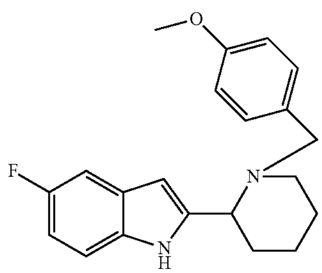 [SMILES: COc1ccc(CN2CCCCC2c2cc3cc(F)ccc3[nH]2)cc1] | 338.42 | 339 | 3.73[1]<br>1.78[2] | ++++ | 5-Fluoro-2-[1-(4-methoxy-benzyl)-piperidin-2-yl]-1H-indole | $^1$H NMR (400 MHz, DMSO) δ 11.38 (s, 1H), 7.52-7.44 (m, 1H), 7.40 (d, J = 9.8 Hz, 1H), 7.21 (d, J = 8.6 Hz, 2H), 7.07-6.91 (m, 3H), 6.77 (s, 1H) 4.47-4.35 (s, 1H), 4.00 (s, 2H), 3.75 (s, 3H), 3.12-2.98 (m, 1H), 2.13 (s, 2H), 1.93-1.80 (s, 2H), 1.78-1.50 (m, 3H). |
| 108 | 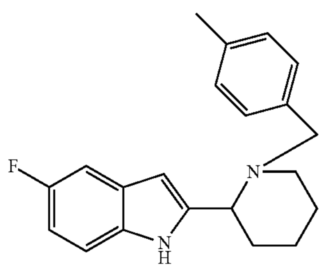 [SMILES: Cc1ccc(CN2CCCCC2c2cc3cc(F)ccc3[nH]2)cc1] | 322.42 | 323 | 3.84[1]<br>1.83[2] | ++++ | 5-Fluoro2-[1-(4-methyl-benzyl)-piperidin-2-yl]-1H-indole | $^1$H NMR (500 MHz, DMSO, TFA salt) δ 11.37 (s, 1H), 9.65 (s, 1H), 7.50-7.46 (s, 1H), 7.39 (d, J = 8.1, 1H), 7.18 (t, J = 12.8, 5H), 7.03 (s, 1H), 6.78 (s, 1H), 4.44 (s, 1H), 4.01 (s, 2H), 3.06 (d, J = 8.4, 2H), 2.30 (s, 4H), 2.14 (s, 2H), 1.86 (d, J = 11.5, 2H), 1.66 (d, J = 58.5, 3H). |
| 109 | 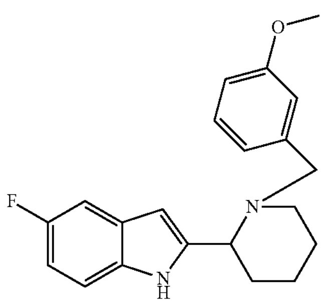 [SMILES: COc1cccc(CN2CCCCC2c2cc3cc(F)ccc3[nH]2)c1] | 338.42 | 339 | 3.73[1]<br>1.77[2] | ++++ | 5-Fluoro-2-[1-(3-methoxy-benzyl)-piperidin-2-yl]-1H-indole | $^1$H NMR (500 MHz, DMSO, TFA salt) δ 11.41 (s, 1H), 9.74 (s, 1H), 7.52-7.28 (m, 3H), 7.08-6 94 (s, 2H), 6.86 (d, J = 7.4, 1H), 6.83-6.75 (d, J = 16.8, 2H), 4.47 (s, 1H), 4.04 (s, 2H), 3.72 (s, 3H), 3.10 (s, 1H), 2.15 (s, 2H), 1.86 (s, 2H), 1.73 (s, 1H), 1.61 (s, 1H). |
| 110 | 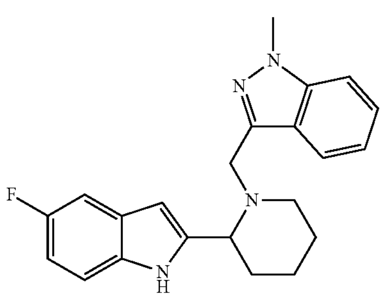 [SMILES: Cn1nc(CN2CCCCC2c2cc3cc(F)ccc3[nH]2)c2ccccc21] | 362.45 | 363 | 3.81[1]<br>1.78[2] | ++++ | 3-[2-(5-Fluoro-1H-indol-2-yl)-piperidin-1-ylmethyl]-1-methyl-1H-indazole | $^1$H NMR (400 MHz, DMSO) δ 11.33 (s, 1H), 10.15 (s, 1H), 7.69 (d, J = 8.6, 1H), 7.57-7.38 (m, 4H), 7.18 (t, J = 7.5, 1H), 7.05 (t, J = 9.1. 1H), 6.83 (s, 1H), 4.58 (s, 1H). 4.50-4.28 (s, 2H), 4.08 (s, 3H), 2.15 (s, 2H), 1.92-1.52 (m, 5H). |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 111 | 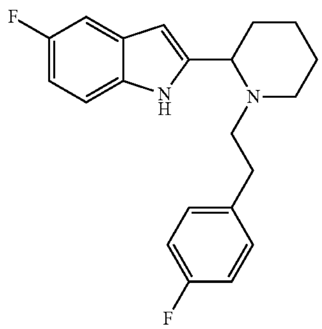 [SMILES: Fc1ccc(CCN2CCCCC2c2cc3cc(F)ccc3[nH]2)cc1] | 340.41 | 341 | 3.89[1]<br>1.90[2] | +++ | 5-Fluoro-2-{1-[2-(4-fluoro-phenyl)-ethyl]-piperidin-2-yl}-1H-indole | 1H NMR (500 MHz, DMSO, TFA exchanged) δ 7.40 (dd, J = 8.9, 4.5 Hz, 1H), 7.26 (dd, J = 9.7, 2.4 Hz, 1H), 7.03-6.98 (m, 2H), 6.93 (t, J = 8.7 Hz, 3H), 6.66 (s, 1H), 4.46 (dd, J = 12.2, 2.7 Hz, 1H), 3.74 (d, J = 12.6 Hz, 1H), 3.25-3.17 (m, 1H), 3.13-2.98 (m, 2H), 2.98-2.88 (m, 1H), 2.58-2.53 (m, 1H), 2.28-2.16 (m, 1H), 2.10 (d, J = 13.6 Hz, 1H), 1.99-1.84 (m, 3H), 1.70-1.58 (m, 1H). |
| 112 | 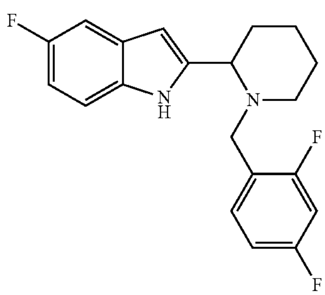 [SMILES: Fc1ccc(CN2CCCCC2c2cc3cc(F)ccc3[nH]2)c(F)c1] | 344.38 | 345 | 3.76[1]<br>1.78[2] | ++++ | 2-[1-(2,4-Difluoro-benzyl)-piperidin-2-yl]-5-fluoro-1H-indole | 1H NMR (500 MHz, DMSO, TFA exchanged) δ 7.49 (dd, J = 8.9, 4.5 Hz, 1H), 7.41 (dd, J = 15.3, 8.3 Hz, 1H), 7.37 (dd, J = 9.7, 2.4 Hz, 1H), 7.20 (t, J = 9.6 Hz, 1H), 7.08 (t, J = 8.4 Hz, 1H), 7.03 (td, J = 9.2, 2.4 Hz, 1H), 6.79 (s, 1H), 4.63 (d, J = 10.6 Hz, 1H), 4.15 (q, J = 13.5 Hz, 2H), 3.43 (d, J = 12.0 Hz, 1H), 3.23 (t, J = 11.9 Hz, 1H), 2.33-2.15 (m, 2H), 1.98-1.62 (m, 4H). |
| 113 | 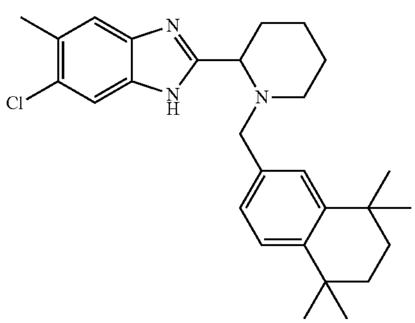 | 450.07 | 451 | 4.05[1]<br>2.27[2] | +++ | 6-Chloro-5-methyl-2-[1-(5,5,8,8-tetramethyl-5,6,7,8-tetrahydro-naphthalen-2-ylmethyl)-piperidin-2-yl]-1H-benzo-imidazole | |
| 114 | 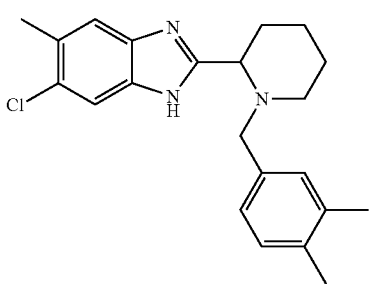 [SMILES: Cc1ccc(CN2CCCCC2c2nc3cc(C)c(Cl)cc3[nH]2)cc1C] | 367.92 | 369 | 3.28[1]<br>1.89[2] | ++++ | 6-Chloro-2-[1-(3,4-dimethyl-benzyl)-piperidin-2-yl]-5-methyl-1H-benzo-imidazole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 115 | 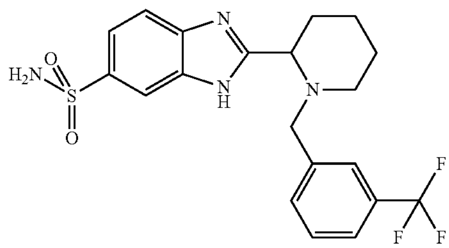 [SMILES: NS(=O)(=O)c1ccc2nc(C3CCCCN3Cc3cccc(C(F)(F)F)c3)[nH]c2c1] | 438.47 | 439 | 2.61[1]<br>1.54[2] | +++ | 2-[1-(3-Trifluoromethyl-benzyl)-piperidin-2-yl]-3H-benzoimidazole-5-sulfonic acid amide | |
| 116 | 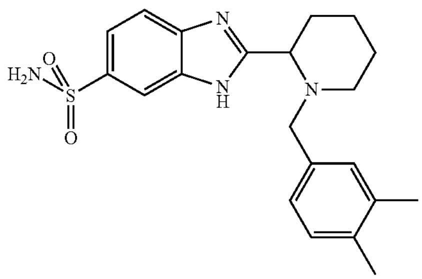 [SMILES: Cc1ccc(CN2CCCCC2c2nc3ccc(S(N)(=O)=O)cc3[nH]2)cc1C] | 398.53 | 400 | 2.32[1]<br>1.44[2] | ++++ | 2-[1-(3,4-Dimethyl-benzyl)-piperidin-2-yl]-3H-benzoimidazole-5-sulfonic acid amide | |
| 117 | 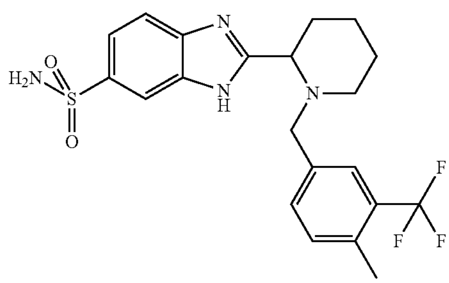 [SMILES: Cc1ccc(CN2CCCCC2c2nc3ccc(S(N)(=O)=O)cc3[nH]2)cc1C(F)(F)F] | 452.50 | 453 | 2.85[1]<br>1.60[2] | +++ | 2-[1-(4-Methyl-3-trifluoromethyl-benzyl)-piperidin-2-yl]-3H-benzoimidazole-5-sulfonic acid amide | |
| 118 | 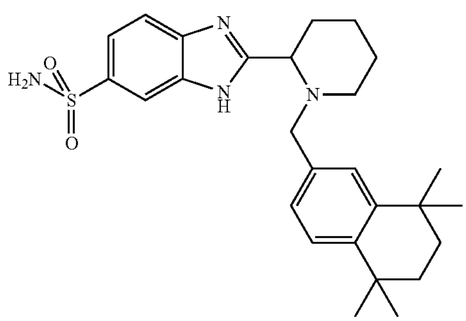 [SMILES: CC1(C)CCC(C)(C)c2cc(CN3CCCCC3c3nc4ccc(S(N)(=O)=O)cc4[nH]3)ccc21] | 480.67 | 482 | 3.36[1]<br>1.89[2] | +++ | 2-[1-(5,5,8,8-Tetramethyl-5,6,7,8-tetrahydro-naphthalen-2-ylmethyl)-piperidin-2-yl]-3H-benzoimidazole-5-sulfonic acid amide | |
| 119 | 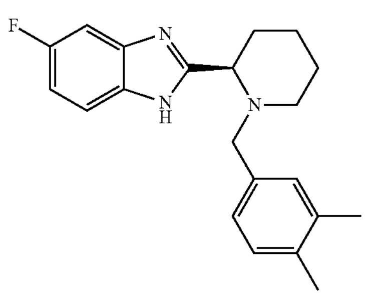 [SMILES: Cc1ccc(CN2CCCC[C@@H]2c2nc3cc(F)ccc3[nH]2)cc1C] | 337.44 | 338 | 3.60[1]<br>1.75[2] | ++++ | 2-[(R)-1-(3,4-Dimethyl-benzyl)-piperidin-2-yl]-5-fluoro-1H-benzoimidazole | $^1$H NMR (400 MHz, DMSO, TFA exchanged) δ 7.73 (dd, J = 8.9, 4.7 Hz, 1H), 7.52 (dd, J = 9.0, 2.4 Hz, 1H), 7.24-7.15 (m, 1H), 7.15-7.06 (m, 3H), 4.76 (d, J = 8.2 Hz, 1H), 4.46-4.18 (m, 2H), 3.57 (d, J = 12.2 Hz, 1H), 3.28-3.17 (m, 1H), 2.37-2.25 (m, 1H), 2.25-2.00 (m, 1H), 2.19 (s, 6H), 1.97-1.85 (m, 3H), 1.77-1.60 (m, 1H). |

TABLE 1-continued

| Example Compound[4] | Chemical Structure | MW [g/mol] | [M + 1]+ | HPLC Rt [min][1,2,3] | IC50 [µM] | Chemical Name | NMR |
|---|---|---|---|---|---|---|---|
| 120 | 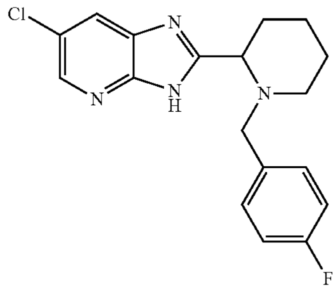 [SMILES: Fc1ccc(CN2CCCCC2c2nc3cc(Cl)cnc3[nH]2)cc1] | 344.82 | 346 | 2.93[1]<br>1.52[2] | ++++ | 6-Chloro-2-[1-(4-fluoro-benzyl)-piperidin-2-yl]-3H-imidazo[4,5-b]pyridine | $^1$H NMR (400 MHz, DMSO) δ 13.10 (s, 1H), 8.29 (d, J = 2.1, 1H), 8.02 (s, 1H), 7.37-7.31 (m, 2H), 7.12-7.05 (m, 2H), 3.66-3.59 (m, 1H), 3.44 (d, J = 13.5, 1H), 3.14 (d, J = 13.6, 1H), 2.90-2.83 (m, 1H), 2.06 (td, J = 11.3, 2.8, 1H), 1.89-1.74 (m, 3H), 1.67-1.58 (m, 1H), 1.57-1.46 (m, 1H), 1.44-1.29 (m, 1H). |
| 121 | 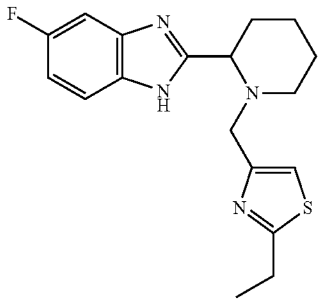 [SMILES: CCc1nc(CN2CCCCC2c2nc3cc(F)ccc3[nH]2)cs1] | 344.46 | 345 | 2.53[1]<br>1.56[2] | ++++ | 2-[1-(2-Ethyl-thiazol-4-ylmethyl)-piperidin-2-yl]-5-fluoro-1H-benzo-imidazole | $^1$H NMR (400 MHz, DMSO) δ 7.68 (dd, J = 8.9, 4.8, 1H), 7.63 (s, 1H), 7.50 (dd, J = 9.3, 2.4, 1H), 7.20-7.13 (m, 1H), 4.67 (s, 1H), 4.33 (q, J = 14.0, 2H), 3.57 (s, 1H), 3.18 (s, 2H), 2.97 (q, J = 7.5, 2H), 2.28-2.00 (m, 2H), 1.93-1.78 (m, 3H), 1.59 (s, 1H), 1.28 (t, J = 7.5, 3H). |
| 122 | 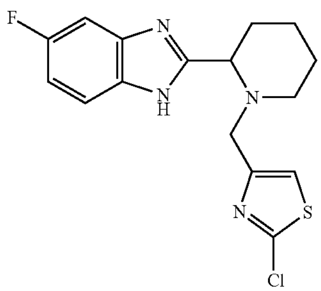 [SMILES: Fc1ccc2[nH]c(C3CCCCN3Cc3csc(Cl)n3)nc2c1] | 350.85 | 352 | 2.45[1]<br>1.49[2] | +++ | 2-[1-(2-Chloro-thiazol-4-ylmethyl)-piperidin-2-yl]-5-fluoro-1H-benzo-imidazole | |
| 123 | 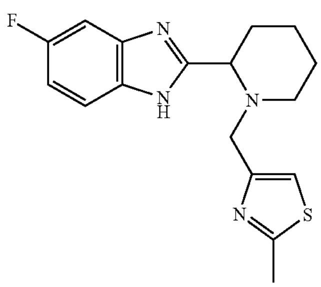 [SMILES: Cc1nc(CN2CCCCC2c2nc3cc(F)ccc3[nH]2)cs1] | 330.43 | 331 | 2.27[1]<br>1.44[2] | +++ | 5-Fluoro-2-[1-(2-methyl-thiazol-4-ylmethyl)-piperidin-2-yl]-1H-benzo-imidazole | |
| 124 | 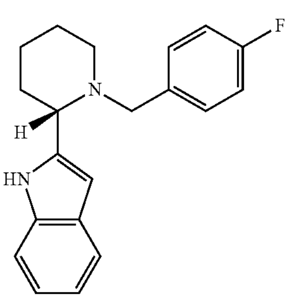 [SMILES: Fc1ccc(CN2CCCC[C@H]2c2cc3ccccc3[nH]2)cc1] | 308.40 | 309 | 3.60[1]<br>1.71[2] | +++ | 2-[(S)-1-(4-Fluoro-benzyl)-piperidin-2-yl]-1H-indole | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 125 | 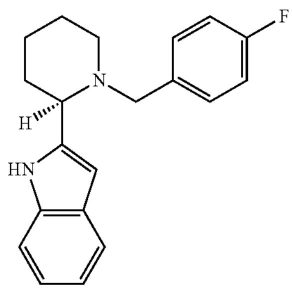 [SMILES: Fc1ccc(CN2CCCC[C@@H]2c2cc3ccccc3[nH]2)cc1] | 308.40 | 309 | 3.65[1]<br>1.72[2] | ++++ | 2-[(R)-1-(4-Fluoro-benzyl)-piperidin-2-yl]-1H-indole | $^1$H NMR (400 MHz, DMSO) δ 11.09 (s, 1H), 7.44 (d, J = 7.7 Hz, 1H), 7.37-7.28 (m, 3H), 7.17-7.05 (m, 2H), 7.01 (t, J = 7.1 Hz, 1H), 6.93 (t, J = 7.0 Hz, 1H), 6.35 (s, 1H), 3.60 (d, J = 13, 1H), 3.17 (d, J = 4.9 Hz, 1H), 2.92 (d, J = 13.4 Hz, 1H), 2.80 (d, J = 11.4 Hz, 1H), 2.01-1.89 (m, 1H), 1.86-1.74 (m, 3H), 1.66-1.28 (m, 3H). |
| 126 | 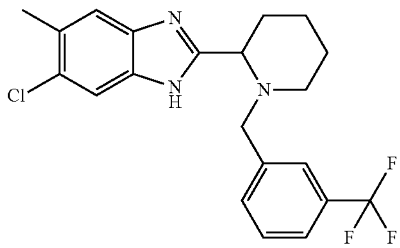 [SMILES: Cc1cc2nc(C3CCCCN3Cc3cccc(C(F)(F)F)c3)[nH]c2cc1Cl] | 407.86 | 409 | 3.65[1]<br>2.02[2] | ++++ | 6-Chloro-5-methyl-2-[1-(3-trifluoro-methyl-benzyl)-piperidin-2-yl]-1H-benzo-imidazole | $^1$H NMR (400 MHz, DMSO) δ 12.46 (d, J = 17.6, 1H), 7.64-7.36 (m, 6H), 3.63-3.58 (m, 1H), 3.55-3.48 (m, 1H), 3.22 (d, J = 13.9, 1H), 2.85 (d, J = 11.6, 1H), 2.39 (s, 3H), 2.08 (td, J = 11.3, 2.7, 1H), 1.89-1.76 (m, 3H), 1.68-1.59 (m, 1H), 1 58-1.46 (m, 1H), 1.44-1.34 (m, 1H). |
| 127 | 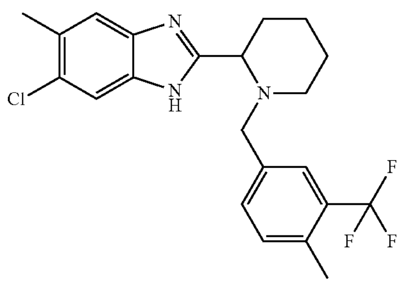 [SMILES: Cc1cc2nc(C3CCCCN3Cc3ccc(C)c(C(F)(F)F)c3)[nH]c2cc1Cl] | 421.89 | 423 | 3.71[1]<br>2.03[2] | +++ | 6-Chloro-5-methyl-2-[1-(4-methyl-3-trifluoro-methyl-benzyl)-piperidin-2-yl]-1H-benzo-imidazole | |
| 128 | 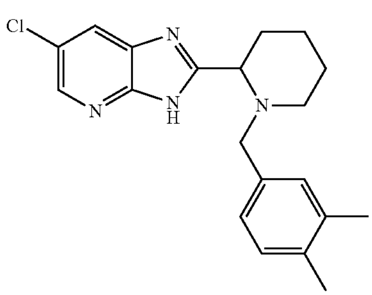 [SMILES: Cc1ccc(CN2CCCCC2c2nc3cc(Cl)cnc3[nH]2)cc1C] | 354.88 | 356 | 3.28[1]<br>1.83[2] | ++++ | 6-Chloro-2-[1-(3,4-dimethyl-benzyl)-piperidin-2-yl]-3H-imidazo[4,5-b]pyridine | $^1$H NMR (400 MHz, DMSO) δ 13.25 (s, 1H), 8.31 (s, 1H), 8.04 (s, 1H), 7.06-6.96 (m, 3H), 3.59 (s, 1H), 3.48 (s, 1H), 3.18 (d, J = 5.1, 1H), 3.04 (d, J = 13.2, 1H), 2.92-2.83 (m, 1H), 2.16 (s, 3H), 2.15 (s, 3H), 2.08-1.98 (m, 1H), 1.87-1.74 (m, 2H), 1.65-1.29 (m, 3H) |
| 129 | 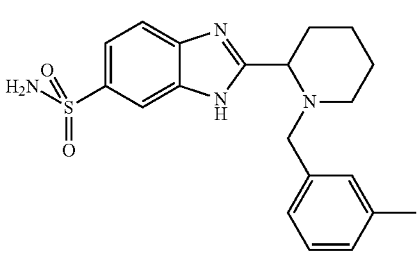 [SMILES: Cc1cccc(CN2CCCCC2c2nc3ccc(S(N)(=O)=O)cc3[nH]2)c1] | 384.50 | 386 | 2.11[1] | ++++ | 2-[1-(3-Methyl-benzyl)-piperidin-2-yl]-3H-benzo-imidazole-5-sulfonic acid amide | |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 130 | 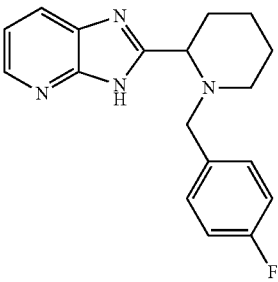 [SMILES: Fc1ccc(CN2CCCCC2c2nc3cccnc3[nH]2)cc1] | 310.37 | 311 | 2.59[1]<br>1.27[2] | ++++ | 2-[1-(4-Fluoro-benzyl)-piperidin-2-yl]-3H-imidazo[4,5-b]pyridine | $^1$H NMR (400 MHz, DMSO) δ 12.99, 12.62 (2xs, 1H), 8.27 (s, 1H), 7.92 (s, 1H), 7.35 (dd, J = 8.5, 5.8, 2H), 7.18 (dd, J = 8.0, 4.8, 1H), 7.09 (t, J = 8.9, 2H), 3.69-3.58 (m, 1H), 3.45 (d, J = 13.6, 2H), 3.13 (d, J = 13.6, 2H), 2.90-2.84 (m, 1H), 2.05 (t, J = 10.1, 1H), 1.92-1.75 (m, 2H), 1.66-1.46 (m, 2H), 1.45-1.32 (m, 1H). |
| 131 | 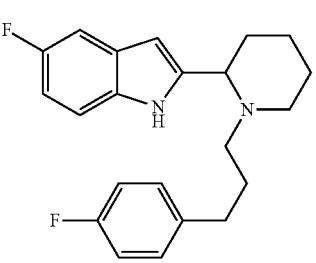 [SMILES: Fc1ccc(CCCN2CCCCC2c2cc3cc(F)ccc3[nH]2)cc1] | 327.38 | 328 | 3.28[1]<br>1.72[2] | +++ | 5-Fluoro-2-[(S)-1-(4-fluoro-benzyl)-piperidin-2-yl]-1H-benzo-imidazole | |
| 132 | 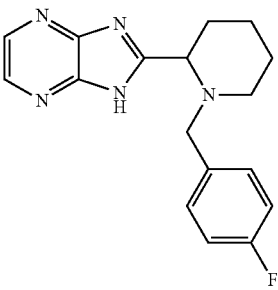 [SMILES: Fc1ccc(CN2CCCCC2c2nc3nccnc3[nH]2)cc1] | 354.44 | 355 | 3.87[1]<br>1.87[2] | ++ | 5-Fluoro-2-{1-[3-(4-fluoro-phenyl)-propyl]-piperidin-2-yl}-1H-indole | |
| 133 | 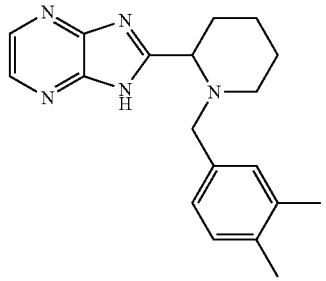 | 311.36 | 312 | 1.68[1]<br>1.25[2] | ++ | 2-[1-(4-Fluoro-benzyl)-piperidin-2-yl]-1H-imidazo[4,5-b]pyrazine | $^1$H NMR (400 MHz, DMSO) δ 13.48 (s, 1H), 8.35 (s, 2H), 7.37 (dd, J = 8.6, 5.7 Hz, 3H), 7.14-7.06 (m, 2H), 3.71-3.65 (m, 1H), 3.48 (d, J = 13.6 Hz, 1H), 3.18 (d, J = 13.6 Hz, 1H), 2.93-2.85 (m, 1H), 2.09 (td, J = 11.2, 2.9 Hz, 1H), 1.94-1.74 (m, 3H), 1.68-1.47 (m, 2H), 1.47-1.32 (m, 1H). |
| 134 | 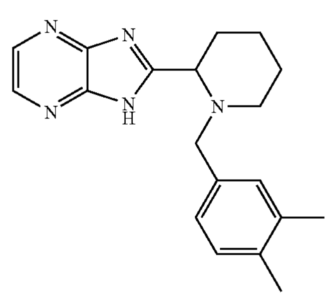 [SMILES: Cc1ccc(CN2CCCCC2c2nc3nccnc3[nH]2)cc1C] | 321.43 | 322 | 2.50[1]<br>1.40[2] | ++++ | 2-[1-(3,4-Dimethyl-benzyl)-piperidin-2-yl]-1H-imidazo[4,5-b]pyrazine | $^1$H NMR (400 MHz, DMSO, d-TFA exchanged) δ 8.46 (s, 2H), 7.22-7.17 (m, 3H), 4.65 (d, J = 10.4, 1H), 4.42 (d, J = 12.9, 1H), 4.11 (d, J = 13.2, 1H), 3.43-3.12 (m, 2H), 2.29-2.12 (m, 8H), 2.08-1.98 (s, 1H), 1.90-1.75 (s, 2H), 1.70-1.55 (m, 1H). |

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 135 | 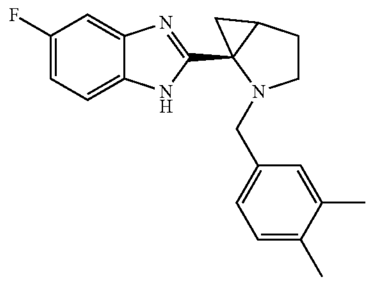 [SMILES: Cc1ccc(CN2CCC3C[C@]32c2nc3cc(F)ccc3[nH]2)cc1C] | 335.42 | 336 | 3.55[1]<br>1.80[2] | ++ | 2-[(R)-2-(3,4-Dimethyl-benzyl)-2-aza-bicyclo-[3.1.0]hex-1-yl]-5-fluoro-1H-benzo-imidazole | |
| 136 | 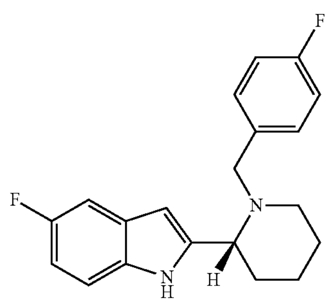 [SMILES: Fc1ccc(CN2CCCC[C@@H]2c2cc3cc(F)ccc3[nH]2)cc1] | 326.39 | 327 | 3.65[1]<br>1.77[2] | ++++ | 5-Fluoro-2-[(R)-1-(4-fluoro-benzyl)-piperidin-2-yl]-1H-indole | $^1$H NMR (500 MHz, DMSO) δ 11.22 (s, 1H), 7.34-7.29 (m, 3H), 7.20 (dd, J = 10.0, 2.5, 1H), 7.10 (t, J = 8.9, 2H), 6.85 (td, J = 9.4, 2.5, 1H), 6.37 (d, J = 1.4, 1H), 3.58 (d, J = 13.4, 1H), 3.43-3.37 (m, 1H), 2.93 (d, J = 13.5, 1H), 2.80 (d, J = 11.6, 1H), 2.00-1.93 (m, 1H), 1.84-1.74 (m, 3H), 1.64-1.57 (m, 1H), 1.54-1.44 (m, 1H), 1.43-1.32 (m, 1H). |
| 137 | 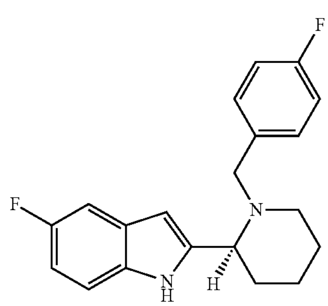 [SMILES: Fc1ccc(CN2CCCC[C@H]2c2cc3cc(F)ccc3[nH]2)cc1] | 326.39 | 327 | 3.71[1]<br>1.74[2] | +++ | 5-Fluoro-2-[(S)-1-(4-fluoro-benzyl)-piperidin-2-yl]-1H-indole | |
| 138 | 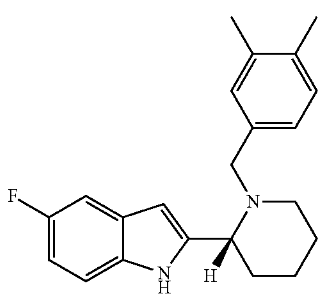 [SMILES: Cc1ccc(CN2CCCC[C@@H]2c2cc3cc(F)ccc3[nH]2)cc1C] | 336.45 | 337 | 4.05[1]<br>1.88[2] | ++++ | 2-[(R)-1-(3,4-Dimethyl-benzyl)-piperidin-2-yl]-5-fluoro-1H-indole | $^1$H NMR (400 MHZ, DMSO, TFA exchanged) δ 7.71 (dd, J = 9.0, 4.7 Hz, 1H), 7.50 (dd, J = 9.0, 2.4 Hz, 1H), 7.26-7.16 (m, 1H), 7.15-7.10 (m, 3H), 4.75 (d, J = 8.1 Hz, 1H), 4.46-4.20 (m, 2H), 3.57 (d, J = 12.1 Hz, 1H), 3.29-3.16 (m, 1H), 2.37-2.24 (m, 1H), 2.25-2.01 (m, 1H), 2.20 (s, 6H), 1.97-1.84 (m, 3H), 1.77-1.60 (m, 1H). |

TABLE 1-continued

| Example Compound[4] | Chemical Structure | MW [g/mol] | [M + 1]+ | HPLC Rt [min][1,2,3] | IC50 [μM] | Chemical Name | NMR |
|---|---|---|---|---|---|---|---|
| 139 | 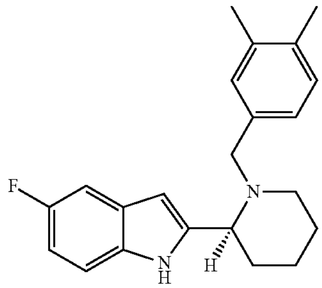 [SMILES: Cc1ccc(CN2CCCC[C@H]2c2cc3cc(F)ccc3[nH]2)cc1C] | 336.45 | 337 | 4.05[1] 1.87[2] | +++ | 2-[(S)-1-(3,4-Dimethyl-benzyl)-piperidin-2-yl]-5-fluoro-1H-indole | $^1$H NMR (400 MHz, DMSO, TFA exchanged) δ 7.70 (dd, J = 8.9, 4.7 Hz, 1H), 7.49 (dd, J = 8.9, 2.4 Hz, 1H), 7.25-7.13 (m, 1H), 7.15-7.05 (m, 3H), 4.75 (d, J = 8.0 Hz, 1H), 4.40-4.20 (m, 2H), 3.57 (d, J = 12.1 Hz, 1H), 3.29-3.12 (m, 1H), 2.37-2.24 (m, 1H), 2.25-2.01 (m, 1H), 2.19 (s, 6H), 1.97-1.84 (m, 3H), 1.77-1.60 (m, 1H). |
| 140 | 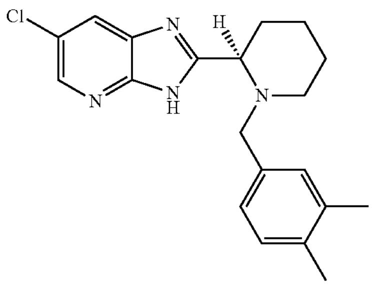 [SMILES: Cc1ccc(CN2CCCC[C@@H]2c2nc3cc(Cl)cnc3[nH]2)cc1C] | 354.88 | 356 | 1.61[2] | +++ | 6-Chloro-2-[(R)-1-(3,4-dimethyl-benzyl)-piperidin-2-yl]-3H-imidazo[4,5-b]pyridine | $^1$H NMR (400 MHz, DMSO) δ 13.2 (s, 1H), 8.31 (s, 1H), 8.07 (s, 1H), 7.06-6.98 (m, 3H), 3.62 (s, 1H), 3.48 (s, 1H), 3.19 (d, J = 5.1, 1H), 3.04 (d, J = 13.2, 1H), 2.94-2.83 (m, 1H), 2.16 (s, 3H), 2.15 (s, 3H), 2.08-1.99 (m, 1H), 1.87-1.74 (m, 2H), 1.65-1.30 (m, 3H). |
| 141 | 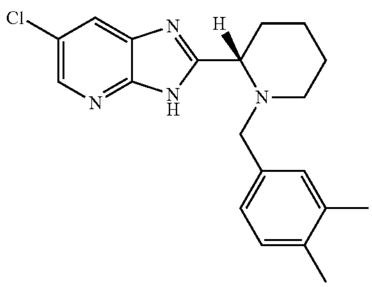 [SMILES: Cc1ccc(CN2CCCC[C@H]2c2nc3cc(Cl)cnc3[nH]2)cc1C] | 354.88 | 356 | 1.54[2] | +++ | 6-Chloro-2-[(S)-1-(3,4-dimethyl-benzyl)-piperidin-2-yl]-3H-imidazo[4,5-b]pyridine | $^1$H NMR (400 MHz, DMSO) δ 13.20 (s, 1H), 8.30 (s, 1H), 8.02 (s, 1H), 7.05-6.94 (m, 3H), 3.59 (s, 1H), 3.45 (s, 1H), 3.18 (d, J = 5.0, 1H), 3.00 (d, J = 13.1, 1H), 2.92-2.81 (m, 1H), 2.13 (s, 3H), 2.11 (s, 3H), 2.10-1.98 (m, 1H), 1.87-1.73 (m, 2H), 1.60-1.24 (m, 3H). |
| 142 | 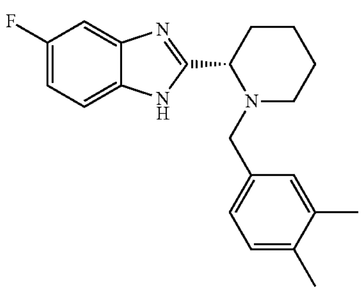 [SMILES: Cc1ccc(CN2CCCC[C@H]2c2nc3cc(F)ccc3[nH]2)cc1C] | 337.44 | 338 | 3.65[1] 1.80[2] | ++++ | 2-[(S)-1-(3,4-Dimethyl-benzyl)-piperidin-2-yl]-5-fluoro-1H-benzo-imidazole | $^1$H NMR (400 MHz, DMSO, TFA exchanged) δ 7.70 (dd, J = 8.9, 4.9 Hz, 1H), 7.48 (dd, J = 9.0, 2.4 Hz, 1H), 7.24-7.11 (m, 1H), 7.17-7.03 (m, 3H), 4.75 (d, J = 8.2 Hz, 1H), 4.46-4.17 (m, 2H), 3.57 (d, J = 12.0 Hz, 1H), 3.28-3.15 (m, 1H), 2.37-2.23 (m, 1H), 2.24-1.96 (m, 1H), 2.19 (s, 6H), 1.96-1.85 (m, 3H), 1.75-1.61 (m, 1H). |
| 143 | 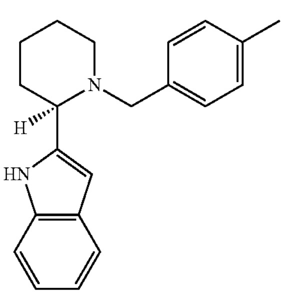 [SMILES: Cc1ccc(CN2CCCC[C@@H]2c2cc3ccccc3[nH]2)cc1] | 304.43 | 305 | 3.79[1] 1.79[2] | ++++ | 2-[(R)-1-(4-Methyl-benzyl)-piperidin-2-yl)-1H-indole | |

TABLE 1-continued

| Example Compound[4] | Chemical Structure | MW [g/mol] | HPLC [M + 1]+ | Rt [min][1,2,3] | IC50 [μM] | Chemical Name | NMR |
|---|---|---|---|---|---|---|---|
| 143 | 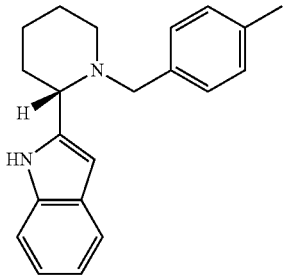 | 304.43 | 305 | 3.79[1]<br>1.79[2] | + | 2-[(S)-1-(4-Methyl-benzyl)-piperidin-2-yl]-1H-indole | |
| 144 | 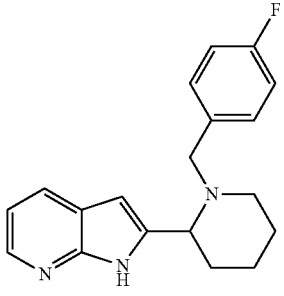 [SMILES: Fc1ccc(CN2CCCCC2c2cc3cccnc3[nH]2)cc1] | 309.39 | 310 | 1.63[1]<br>1.54[2] | +++ | 2-[1-(4-Fluoro-benzyl)-piperidin-2-yl]-1H-pyrrolo[2,3-b]pyridine | 1H NMR (400 MHz, DMSO) δ 11.79 (s, 1H), 8.30 (dd, J = 4.7, 1.5, 1H), 8.05 (dd, J = 7.9, 1.5, 1H), 7.36 (dd, J = 8.6, 5.5, 2H), 7.24 (dd, J = 9.8, 7.6, 2H), 7.17-7.11 (m, 1H), 6.80 (s, 1H), 4.45 (s, 1H), 4.16-4.02 (m, 2H), 3.15-3.05 (m, 2H), 2.15 (s, 1H), 1.93-1.83 (m, 2H), 1.80-1.53 (m, 3H). |

[1]HPLC method (non polar)
Solvent A: Water + 0.1% TFA
Solvent B: Acetonitril + 0.08% TFA
Flow: 1.5 ml/min
Gradient: 0.0 min 20% B
5.0 min 100% B
5.5 min 100% B
6.0 min 20% B
6.5 min 20% B
Column: Chromolith Performance RP18e 100-3
[2]HPLC method (polar)
Solvent A: Water + 0.05% Formic Acid
Solvent B: Acetonitril + 0.04% Formic Acid
Flow: 2,4 ml/min, Wavelength: 220 nm
Gradient: 0.0 min 4% B
2.8 min 100% B
3.3 min 100% B
3.4 min 4% B
Column: Chromolith Speed ROD RP18e 50-4.6 mm
[3]HPLC/MS
Solvent A: Water + 0.1% TFA
Solvent B: Acetonitril + 0.1% TFA
Flow: 2 ml/min, Wavelength: 254 nm
Gradient: 0 min 5% B
8 min 100% B
8.1 min 10% B
Column: Chromolith Speed ROD RP18e 50-4.6 mm
[4]Example numbers 11, 12, 43, 53, 77, 78, and 80 were omitted intentionally
$IC_{50}$ < 0.5 μM "++++"
0.5 μM ≤ $IC_{50}$ ≤ 5 μM "+++"
5 μM < $IC_{50}$ ≤ 15 μM "++"
$IC_{50}$ > 15 μM "+"

The invention claimed is:
1. A compound of Formula (I)

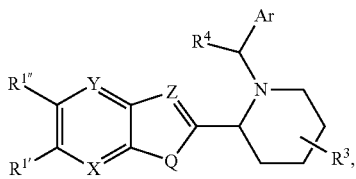

or its stereoisomers or tautomers, or pharmaceutically acceptable salts of each of the foregoing, including mixtures thereof in all ratios, wherein $R^{1'}$, $R^{1'''}$, $R^2$, $R^4$, are each independently H, Hal, OH, CN, $NO_2$, $NH_2$, LA, NH(LA), $N(LA)_2$, COOH, COO(LA), $SO_2(LA)$, O(LA), $SO_2NH_2$, $SO_2NH(LA)$, $SO_2N(LA)_2$, $R^{5'}$, $R^{5'''}$ are each independently Hal, OH, CN, $NO_2$, $NH_2$, LA, NH(LA), $N(LA)_2$, COO(LA), $SO_2(LA)$, O(LA), $SO_2NH_2$, $SO_2NH(LA)$, $SO_2N(LA)_2$, X, Y, Z are each independently CH, or C(Hal),
Q is NH,
each LA is independently unbranched or branched alkyl having 1, 2, 3 or 4 carbon atoms, wherein one, two or three H atoms may be replaced by Hal,
$R^3$ is H or LA,
Ar is a mono- or bicyclic aromatic homo- or heterocycle having 0, 1, 2, 3 or 4 N, O and/or S atoms and 5, 6, 7, 8, 9, or 10 skeleton atoms, which is mono-, or disubstituted by $R^{5'}$, $R^{5'''}$,
Hal is F, Cl, Br or I,
with the proviso that said compound is not
3-ethyl-2-1[-(phenylmethyl)-2-piperidinyl]-1 H-indole.

2. The compound according to claim 1, or its stereoisomers or tautomers, or pharmaceutically acceptable salts of each of the foregoing, including mixtures thereof in all ratios, of Formula (I')

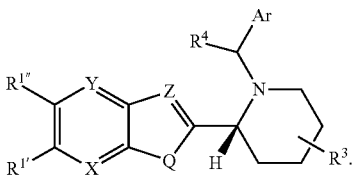

3. The compound according to claim 1, or its stereoisomers or tautomers, or pharmaceutically acceptable salts of each of the foregoing, including mixtures thereof in all ratios, wherein, $R^{1'}$ and $R^{1'''}$ are each independently H, methyl, F, Cl, Br or $SO_2NH_2$.

4. The compound according to claim 1, wherein the compound is selected from the group consisting of:
2-[1-(2-Ethyl-thiazol-4-ylmethyl)-piperidin-2-yl]-5-fluoro-1H-indole,
2-[(R)-1-(3,4-Dimethyl-benzyl)-piperidin-2-yl]-5-fluoro-1H-indole,
2-[1-(3-Methyl-benzyl)-piperidin-2-yl]-1H-indole,
2-[1 -(4-Fluoro-benzyl)-piperidin-2-yl]-1H-indole,
5-Chloro-2-[1-(4-methoxy-benzyl)-piperidin-2-yl]-1H-indole,
2-[(R)-1-(4-Fluoro-benzyl)-piperidin-2-yl]-1H-indole,
5-Fluoro-2-[(R)-1-(4-fluoro-benzyl)-piperidin-2-yl]-1H-indole,
5-Fluoro-2-[1-(3-methoxy-benzyl)-piperidin-2-yl]-1H-indole,
5-Fluoro-2-[1-(4-fluoro-benzyl)-6-methyl-piperidin-2-yl]-1H-indole,
5-Fluoro-2-[1-(4-methoxy-benzyl)-piperidin-2-yl]-1H-indole,
5-Fluoro-2-[1-(4-methyl-benzyl)-piperidin-2-yl]-1H-indole,
5-Fluoro-2-[6-methyl-1-(3-methyl-benzyl)-piperidin-2-yl]-1H-indole,
5-Fluoro-2-[6-methyl-1-(5-methyl-furan-2-ylmethyl)-piperidin-2-yl]-1H-indole,
5-Methoxy-2-[1-(3-methoxy-benzyl)-piperidin-2-yl]-1H-indole;
2-[1-(4-Methoxy-benzyl)-piperidin-2-yl]-1H-indole;
2-[1-(3-Methoxy-benzyl)-piperidin-2-yl]-1H-indole;
2-[1-(3,4-Dimethyl-benzyl)-piperidin-2-yl]-1H-indole;
2-(1-Benzyl-piperidin-2-yl)-1H-indole;
2-[1-(2,3-Difluoro-benzyl)-piperidin-2-yl]-1H-indole;
3-[2-(1H-indol-2-yl)-piperidin-1-ylmethyl]-1-methyl-1H-indol;
3-[2-(1H-indol-2-yl)-piperidin-1-ylmethyl]-1-isopropyl-1H-indol;
2-[1-(4-Methyl-benzyl)-piperidin-2-yl]-1H-indole;
5-Fluoro-2-[1-(3-methyl-benzyl)-piperidin-2-yl]-1H-indole;
2-[1-(3,4-Dimethyl-benzyl)-piperidin-2-yl]-5-fluoro-1H-indole;
2-[1-(4-Trifluoromethyl-benzyl)-piperidin-2-yl]-1H-indole;
7-Methyl-2-[1-(3-methyl-benzyl)-piperidin-2-yl]-1H-indole;
2-[1-(3,4-Dimethyl-benzyl)-piperidin-2-yl]5,7-difluoro-1H-indole;
2-[1-(3,4-Dimethyl-benzyl)-piperidin-2-yl]4,7-difluoro-1H-indole;
4-[2-(1H-indol-2-yl)-piperidin-1-ylmethyl]-benzoic acid ethyl ester;
2-[2-(1H-indol-2-yl)-6-methyl-piperidin-1-ylmethyl]-phenol;
2-[1-(3,4-Dimethyl-benzyl)-6-methyl-piperidin-2-yl]-1H-indole;
5-Fluoro-2-[1-(2-methoxy-benzyl)-6-methyl-piperidin-2-yl]-1H-indole;
2-[2-(5-Fluoro-1H-indol-2-yl)-6-methyl-piperidin-1-ylmethyl]phenol;
5-Fluoro-2-[6-methyl-1-(3-nitro-benzyl)-piperidin-2-yl]-1H-indole;
4-[2-(5-Fluoro-1H-indol-2-yl)-6-methyl-piperidin-1-ylmethyl]-benzonitrile;
5-Fluoro-2-[1-(4-methanesulfonyl-benzyl)-6-piperidin-2-yl]-1H-indole;
2-[1-(4-Ethoxy-benzyl)-6-methyl-piperidin-2-yl]-5-fluoro-1H-indole;
4-[2-(5-Fluoro-1H-indol-2-yl)-6-methyl-piperidin-1-ylmethyl]-benzoic acid ethyl ester;
2-[1-(2,4-Difluoro-benzyl)-6-methyl-piperidin-2-yl]-5-fluoro-1H-indole;
2-[1-(4-Chloro-benzyl)-6-methyl-piperidin-2-yl]-5-fluoro-1-H-indole;
5-Fluoro-2-[1-(3-methoxy-benzyl)-6-methyl-piperidin-2-yl]-1H-indole,
5-Fluoro-2-(6-methyl-1-pyridin-3-ylmethyl-piperidin-2-yl)-1H -indole;

5-Fluoro-2-[6-methyl-1-(4-methyl-benzyl)-piperidin-2-yl]-1H-indole,
2-[1-(2,3-Dichloro-benzyl)-piperidin-2-yl]-5-fluoro-1H-indole;
2-[1-(3,5-Dimethoxy-benzyl)-piperidin-2-yl]-5-fluoro-1H-indole;
5-Fluoro-2-(1-pyridin-2-ylmethyl-piperidin-2-yl) -1H-indole;
2-[1-(3-Bromo-benzyl)-piperidin-2-yl]-5-fluoro-1H-indole;
2-[1-(4-Bromo-benzyl)-piperidin-2-yl]-5-fluoro-1H-indole;
5-Fluoro-2-[1-(4-fluoro-benzyl)-5-methyl-piperidin-2-yl]-1H-indole;
5-Fluoro-2-[1-(1H-indol-3-ylmethyl)-piperidin-2-yl]-1H-indole;
5-Fluoro-2-[1-(4-methoxy-benzyl)-4-methyl-piperidin-2-yl]-1H-indole;
3-[2-(5-Fluoro-1H-indol-2-yl)-piperidin-1-ylmethyl]1,5-dimethyl-1H-indole;
3-[2-(5-Fluoro-1H-indol-2-yl)-piperidin-1-ylmethyl]1,6-dimethyl-1H-indole;
2-[1-(4-Bromo-benzyl)-piperidin-2-yl]-1H-indole;
2-[1-(4-Methoxy-benzyl)-4-methyl-piperidin-2-yl]-1H-indole;
2-[1-(4-Fluoro-benzyl)-piperidin-2-yl]-4,6-dimethyl-1H-indole;
2-[1-(4-Fluoro-benzyl)-piperidin-2-yl]-5-methyl-1H-indole;
2-[1-(3-Methoxy-benzyl)-piperidin-2-yl]-5-methyl-1H-indole;
5-Fluoro-2-{1-[1-(4-fluoro-phenyl)-ethyl]-piperidin-2-yl}-1H-indole;
5-Chloro-2-[1-(3-methoxy-benzyl)-4-methyl-piperidin-2-yl]-1H-indole;
5-Fluoro-2-[1-(4-fluoro-benzyl)-piperidin-2-yl]-3-methyl-1H-indole;
2-[1-(3,4-Dimethyl-benzyl)-4-methyl-piperidin-2-yl]-1H-indole;
2-[1-(4-Fluoro-benzyl)-3-methyl-piperidin-2-yl]-1H-indole;
2-[1-(3,4-Dimethyl-benzyl)-4-methyl-piperidin-2-yl]-5-methoxy-1H-indole;
2-[1-(3,5-Dimethyl-benzyl)-piperidin-2-yl]-5-fluoro-1H-indole;
3-[2-(5-Fluoro-1H-indol-2-yl)-piperidin-1-ylmethyl]berizonitrile
2-[1-(3,4-Dimethyl-benzyl)-4-methyl-piperidin-2-yl]-5-fluoro-1H-indole;
3-[2-(5-Fluoro-1H-indol-2-yl)-piperidin-1-ylmethyl]-1-methyl-1H-indazole;
2-[1-(2,4-Difluoro-benzyl)-piperidin-2-yl]-5-fluoro-1H-indole;
2-[(S)-1-(4-Fluoro-benzyl)-piperidin-2-yl]-1H-indole;
5-Fluoro-2-[(S)-1-(4-fluoro-benzyl)-piperidin-2yl]-1H-indole;
2-[(S)-1-(3,4-Dimethyl-benzyl)-piperidin-2-yl]-5-fluoro-1H-indole;
2-[(R)-1-(4-Methyl-benzyl)-piperidin-2-yl]-1H-indole;
or its stereoisomers or tautomers, or pharmaceutically acceptable salts of each of the foregoing, including mixtures thereof in all ratios.

5. The compound according to claim 1, or its stereoisomers or tautomers, or pharmaceutically acceptable salts of each of the foregoing, including mixtures thereof in all ratios, wherein $R^4$ is H or methyl.

6. The compound according to claim 1, or its stereoisomers or tautomers, or pharmaceutically acceptable salts of each of the foregoing, including mixtures thereof in all ratios, wherein $R^3$ is H or methyl.

7. The compound according to claim 1, or its stereoisomers or tautomers, or pharmaceutically acceptable salts of each of the foregoing, including mixtures thereof in all ratios, wherein Ar is phenyl, furyl, pyridyl, thiazolyl or indazolyl.

8. The compound according to claim 1, or its stereoisomers or tautomers, or pharmaceutically acceptable salts of each of the foregoing, including mixtures thereof in all ratios, wherein $R^{5'}$ and $R^{5''}$ are each independently F, methyl, ethyl, methoxy, trifluoromethyl, hydroxy or nitro.

9. The compound according to claim 1, or its stereoisomers or tautomers, or pharmaceutically acceptable salts of each of the foregoing, including mixtures thereof in all ratios, wherein
$R^{1'}$, $R^{1''}$ are each independently H, methyl, F, CI, Br or $SO_2NH_2$,
$R^3$ is H or methyl,
$R^4$ is H or methyl,
Ar is phenyl, furyl, pyridyl, thiazolyl or indazolyl,
$R^{5'}$, $R^{5''}$ are each independently F, methyl, ethyl, methoxy, trifluoromethyl, hydroxy or nitro.

10. The compound according to claim 1, or its stereoisomers or tautomers, or pharmaceutically acceptable salts of each of the foregoing, including mixtures thereof in all ratios, wherein
Q is NH,
$R^2$ is H, methyl or isopropyl,
Z is CH.

11. The compound according to claim 1, or its stereoisomers or tautomers, or pharmaceutically acceptable salts of each of the foregoing, including mixtures thereof in all ratios, wherein
Y is CH, or C—F,
X is CH.

12. The compound according to claim 1, or its stereoisomers or tautomers, or pharmaceutically acceptable salts of each of the foregoing, including mixtures thereof in all ratios, wherein
Q is NH,
Z is CH,
$R^{1'}$ is H,
$R^{1''}$ is F.

13. The compound according to claim 1, or its stereoisomers or tautomers, or pharmaceutically acceptable salts of each of the foregoing, including mixtures thereof in all ratios, wherein
$R^3$ is H,
$R^4$ is H,
Ar is phenyl,
$R^{5'}$, $R^{5''}$ are independently F or methyl,
Q is NH,
Y is CH.

14. A pharmaceutical composition comprising a compound according to claim 1, or its stereoisomers or tautomers, or pharmaceutically acceptable salts of each of the foregoing, including mixtures thereof in all ratios, as an active ingredient, together with a pharmaceutically acceptable carrier.

15. A method for treating an inflammatory disease, comprising administering to a subject a compound of claim 1, or its stereoisomers or tautomers, or pharmaceutically acceptable salts of each of the foregoing, including mixtures thereof in all ratios.

16. The method of claim 15, wherein the disease is selected from the group consisting of benign hyperplasia of the skin, restenosis, diabetic retinopathy, macular degeneration, fibrosis, pancreatitis, arthritis, and psoriasis.

* * * * *